US012016996B2

(12) United States Patent
Hepworth et al.

(10) Patent No.: US 12,016,996 B2
(45) Date of Patent: *Jun. 25, 2024

(54) RECEPTACLE SECTION

(71) Applicant: NICOVENTURES TRADING LIMITED, London (GB)

(72) Inventors: Richard Hepworth, Southampton (GB); Colin Dickens, London (GB)

(73) Assignee: NICOVENTURES TRADING LIMITED, London (GB)

(*) Notice: Subject to any disclaimer, the term of this patent is extended or adjusted under 35 U.S.C. 154(b) by 612 days.

This patent is subject to a terminal disclaimer.

(21) Appl. No.: 16/333,567

(22) PCT Filed: Sep. 12, 2017

(86) PCT No.: PCT/EP2017/072814
§ 371 (c)(1),
(2) Date: Mar. 14, 2019

(87) PCT Pub. No.: WO2018/050613
PCT Pub. Date: Mar. 22, 2018

(65) Prior Publication Data
US 2019/0254344 A1    Aug. 22, 2019

(30) Foreign Application Priority Data

Sep. 14, 2016  (GB) .................................. 1615603

(51) Int. Cl.
*A24D 3/06*         (2006.01)
*A24F 7/00*         (2006.01)
(Continued)

(52) U.S. Cl.
CPC ............. *A61M 11/042* (2014.02); *A24F 7/00* (2013.01); *A24F 40/30* (2020.01); *A24F 40/40* (2020.01);
(Continued)

(58) Field of Classification Search
None
See application file for complete search history.

(56) References Cited

U.S. PATENT DOCUMENTS 3,894,544 A    7/1975  Egri
4,338,931 A    7/1982  Cavazza
(Continued)

FOREIGN PATENT DOCUMENTS

AR       089648 A1    9/2014
AR       091949 A1    3/2015
(Continued)

OTHER PUBLICATIONS

International Search Report, Application No. PCT/EP2017/07281, dated Nov. 22, 2017, 3 pages.
(Continued)

*Primary Examiner* — Katherine A Will
(74) *Attorney, Agent, or Firm* — Husch Blackwell LLP

(57) ABSTRACT

A receptacle section for an aerosol provision article is described. The aerosol provision article is for generating a flow of aerosol in use. The receptacle section is arranged for receiving therein an activatable element for modifying, once activated, a property of the flow of aerosol. The receptacle section includes at least one activating element operable to apply, after an installation of the activatable element in the receptacle section by a user, a force to the activatable element to activate the activatable element installed in the receptacle section in use.

18 Claims, 12 Drawing Sheets

Figure 1:
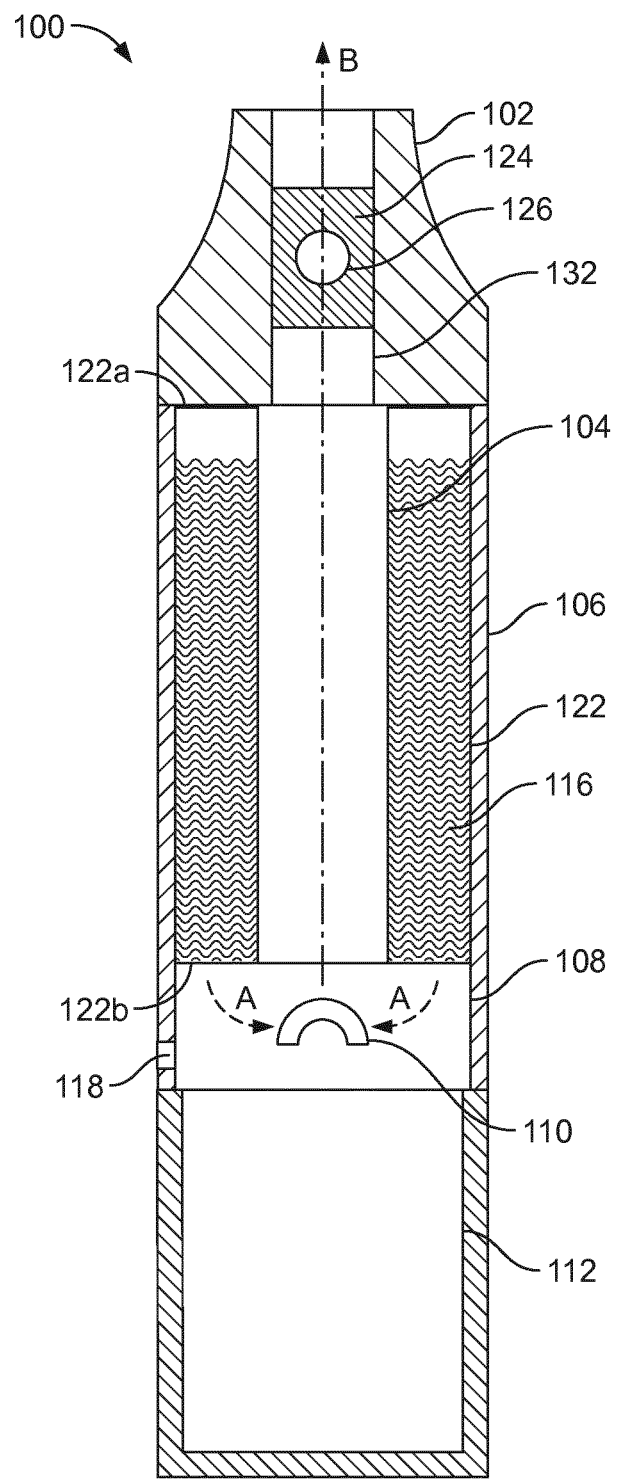

(51) Int. Cl.
*A24F 40/30* (2020.01)
*A24F 40/40* (2020.01)
*A61M 11/04* (2006.01)
*A61M 15/06* (2006.01)
*A24F 40/10* (2020.01)

(52) U.S. Cl.
CPC .............. *A61M 15/06* (2013.01); *A24D 3/061* (2013.01); *A24F 40/10* (2020.01); *A61M 2205/3653* (2013.01); *A61M 2205/8206* (2013.01)

(56) References Cited

U.S. PATENT DOCUMENTS

| | | | |
|---|---|---|---|
| 4,714,082 A | 12/1987 | Banerjee et al. | |
| 5,099,861 A | 3/1992 | Clearman et al. | |
| 5,632,287 A | 5/1997 | Hayworth et al. | |
| 6,382,465 B1 | 5/2002 | Greiner-Perth | |
| 6,606,992 B1 | 8/2003 | Schuler et al. | |
| 6,705,313 B2 | 3/2004 | Niccolai | |
| 6,708,846 B1 | 3/2004 | Fuchs et al. | |
| 7,726,320 B2 | 6/2010 | Robinson et al. | |
| 8,377,009 B2 | 2/2013 | Sullivan et al. | |
| 8,499,766 B1 | 8/2013 | Newton | |
| 8,997,753 B2 | 4/2015 | Li et al. | |
| 8,997,754 B2 | 4/2015 | Tucker et al. | |
| 9,004,073 B2 | 4/2015 | Tucker et al. | |
| 9,247,773 B2 | 2/2016 | Memari et al. | |
| 9,282,772 B2 | 3/2016 | Tucker et al. | |
| 9,693,587 B2 | 7/2017 | Plojoux et al. | |
| 10,010,687 B2 | 7/2018 | Von Schuckmann | |
| 10,015,990 B2 | 7/2018 | Mironov | |
| 10,172,390 B2 | 1/2019 | Nakano et al. | |
| 10,368,583 B2 | 8/2019 | Takeuchi et al. | |
| 10,426,199 B2 | 10/2019 | Turner et al. | |
| 10,470,491 B2 | 11/2019 | Sutton et al. | |
| 10,492,526 B2 | 12/2019 | Sampson et al. | |
| 10,758,686 B2 | 9/2020 | Reevell | |
| 2004/0173229 A1 | 9/2004 | Crooks et al. | |
| 2005/0000518 A1 | 1/2005 | Dunkley et al. | |
| 2005/0016533 A1 | 1/2005 | Schuler | |
| 2005/0022813 A1 | 2/2005 | Alston | |
| 2005/0048003 A1 | 3/2005 | Ohki et al. | |
| 2005/0056280 A1 | 3/2005 | Alston et al. | |
| 2005/0081852 A1 | 4/2005 | Rangachari | |
| 2005/0150492 A1 | 7/2005 | Dunkley et al. | |
| 2007/0012327 A1 | 1/2007 | Karles et al. | |
| 2007/0186945 A1 | 8/2007 | Olegario et al. | |
| 2008/0092912 A1 | 4/2008 | Robinson et al. | |
| 2010/0101589 A1 | 4/2010 | Nelson et al. | |
| 2010/0154808 A1 | 6/2010 | Boll et al. | |
| 2011/0126848 A1 | 6/2011 | Zuber et al. | |
| 2013/0042865 A1 | 2/2013 | Monsees et al. | |
| 2013/0068081 A1 | 3/2013 | Kronberg et al. | |
| 2013/0121608 A1 | 5/2013 | Winnemoeller et al. | |
| 2013/0192615 A1 | 8/2013 | Tucker et al. | |
| 2013/0192616 A1 | 8/2013 | Tucker et al. | |
| 2013/0192619 A1 | 8/2013 | Tucker et al. | |
| 2013/0192620 A1 | 8/2013 | Tucker et al. | |
| 2013/0192621 A1 | 8/2013 | Li et al. | |
| 2013/0192622 A1 | 8/2013 | Tucker et al. | |
| 2013/0192623 A1 | 8/2013 | Tucker et al. | |
| 2013/0298905 A1 | 11/2013 | Levin et al. | |
| 2013/0312742 A1 | 11/2013 | Monsees et al. | |
| 2014/0060554 A1 | 3/2014 | Collett et al. | |
| 2014/0202478 A1 | 7/2014 | Awty et al. | |
| 2014/0202479 A1* | 7/2014 | Nicholls | A24D 3/04 131/337 |
| 2014/0326260 A1 | 11/2014 | Gladden et al. | |
| 2014/0332014 A1* | 11/2014 | Penrose | A24D 3/048 131/331 |
| 2015/0027469 A1 | 1/2015 | Tucker et al. | |
| 2015/0027477 A1 | 1/2015 | Yoshino et al. | |
| 2015/0083150 A1 | 3/2015 | Conner et al. | |
| 2015/0245654 A1 | 9/2015 | Memari et al. | |
| 2015/0245655 A1 | 9/2015 | Memari et al. | |
| 2015/0245656 A1 | 9/2015 | Memari et al. | |
| 2015/0245657 A1 | 9/2015 | Memari et al. | |
| 2015/0245662 A1 | 9/2015 | Memari et al. | |
| 2015/0245663 A1 | 9/2015 | Memari et al. | |
| 2015/0245664 A1 | 9/2015 | Memari et al. | |
| 2015/0245665 A1 | 9/2015 | Memari et al. | |
| 2015/0245666 A1 | 9/2015 | Memari et al. | |
| 2015/0245667 A1 | 9/2015 | Memari et al. | |
| 2015/0245668 A1 | 9/2015 | Memari et al. | |
| 2015/0313281 A1 | 11/2015 | Bonici et al. | |
| 2015/0359266 A1 | 12/2015 | Memari et al. | |
| 2015/0374035 A1 | 12/2015 | Sanchez et al. | |
| 2016/0007648 A1 | 1/2016 | Sutton et al. | |
| 2016/0037823 A1* | 2/2016 | Ruben | A24D 3/061 131/337 |
| 2016/0206004 A1 | 7/2016 | Shinkawa et al. | |
| 2017/0347706 A1 | 12/2017 | Aoun et al. | |
| 2017/0360088 A1 | 12/2017 | Pijnenburg et al. | |
| 2018/0027882 A1 | 2/2018 | Hepworth et al. | |
| 2018/0279678 A1 | 10/2018 | Hepworth et al. | |
| 2018/0360122 A1 | 12/2018 | Aoun et al. | |
| 2019/0098930 A1 | 4/2019 | Fallon et al. | |
| 2019/0125988 A1 | 5/2019 | Trzecieski | |
| 2019/0230990 A1 | 8/2019 | Hepworth | |
| 2019/0254343 A1 | 8/2019 | Hepworth et al. | |
| 2019/0254345 A1 | 8/2019 | Hepworth et al. | |
| 2020/0046026 A1 | 2/2020 | Pijnenburg et al. | |
| 2020/0060333 A1 | 2/2020 | Sutton et al. | |
| 2020/0390149 A1 | 12/2020 | Hepworth et al. | |

FOREIGN PATENT DOCUMENTS

| | | |
|---|---|---|
| AU | 2013214984 A1 | 8/2014 |
| AU | 2013214987 A1 | 8/2014 |
| AU | 2013214991 A1 | 8/2014 |
| AU | 2013214993 A1 | 8/2014 |
| AU | 2013214994 A1 | 8/2014 |
| AU | 2013214997 A1 | 8/2014 |
| AU | 2013214998 A1 | 8/2014 |
| CA | 2845090 A1 | 2/2013 |
| CA | 2862105 A1 | 8/2013 |
| CA | 2862294 A1 | 8/2013 |
| CA | 2863185 A1 | 8/2013 |
| CA | 2863189 A1 | 8/2013 |
| CA | 2867620 A1 | 8/2013 |
| CA | 2867624 A1 | 8/2013 |
| CA | 2868313 A1 | 8/2013 |
| CN | 2760984 Y | 3/2006 |
| CN | 104219973 A | 12/2014 |
| CN | 104244749 A | 12/2014 |
| CN | 104244750 A | 12/2014 |
| CN | 104284606 A | 1/2015 |
| CN | 104302197 A | 1/2015 |
| CN | 104394722 A | 3/2015 |
| CN | 204275207 U | 4/2015 |
| CN | 104661544 A | 5/2015 |
| CN | 204560971 | 8/2015 |
| CN | 104968225 A | 10/2015 |
| DE | 60310596 T2 | 10/2007 |
| EA | 201490448 A1 | 12/2014 |
| EP | 1555899 B1 | 12/2006 |
| EP | 2083643 A1 | 8/2009 |
| EP | 2723429 A1 | 4/2014 |
| EP | 2727619 A2 | 5/2014 |
| EP | 2740506 A1 | 6/2014 |
| EP | 2740507 A1 | 6/2014 |
| EP | 2740508 A1 | 6/2014 |
| EP | 2727619 A3 | 7/2014 |
| EP | 2756859 A1 | 7/2014 |
| EP | 2756860 A1 | 7/2014 |
| EP | 2809180 A1 | 12/2014 |
| EP | 2809182 A2 | 12/2014 |
| EP | 2809183 A1 | 12/2014 |
| EP | 2809184 A1 | 12/2014 |
| EP | 2809185 A1 | 12/2014 |
| EP | 2809186 A1 | 12/2014 |
| EP | 2809187 A1 | 12/2014 |

(56) References Cited

FOREIGN PATENT DOCUMENTS

| | | |
|---|---|---|
| EP | 2723429 A4 | 4/2015 |
| EP | 2809180 A4 | 7/2015 |
| EP | 2809184 A4 | 7/2015 |
| EP | 2809187 A4 | 7/2015 |
| EP | 2809182 A4 | 8/2015 |
| EP | 2809183 A4 | 8/2015 |
| EP | 2809185 A4 | 8/2015 |
| EP | 2809186 A4 | 9/2015 |
| EP | 2948006 A1 | 12/2015 |
| EP | 2964038 A1 | 1/2016 |
| EP | 2975956 A1 | 1/2016 |
| EP | 3039972 A1 | 7/2016 |
| GB | 2394394 A | 4/2004 |
| GB | 201413018 | 9/2014 |
| GB | 201413019 | 9/2014 |
| GB | 201413021 | 9/2014 |
| GB | 201413025 | 9/2014 |
| GB | 201413027 | 9/2014 |
| GB | 201413028 | 9/2014 |
| GB | 201413030 | 9/2014 |
| GB | 201413032 | 9/2014 |
| GB | 201413034 | 9/2014 |
| GB | 201413036 | 9/2014 |
| GB | 201413037 | 9/2014 |
| GB | 2513061 A | 10/2014 |
| GB | 2523585 A | 9/2015 |
| GB | 2523585 A8 | 9/2015 |
| GB | 2525080 A | 10/2015 |
| GB | 2525294 A | 10/2015 |
| GB | 2525295 A | 10/2015 |
| GB | 2525480 A | 10/2015 |
| GB | 2525722 A | 11/2015 |
| GB | 2525723 A | 11/2015 |
| GB | 2525724 A | 11/2015 |
| GB | 2525725 A | 11/2015 |
| GB | 2525726 A | 11/2015 |
| GB | 2525727 A | 11/2015 |
| GB | 2529919 A | 3/2016 |
| GB | 2531633 A | 4/2016 |
| HK | 1197203 A1 | 1/2015 |
| HK | 1198138 A1 | 3/2015 |
| HK | 1198142 A1 | 3/2015 |
| HK | 1198143 A1 | 3/2015 |
| HK | 1200128 A1 | 7/2015 |
| HK | 1200129 A1 | 7/2015 |
| HK | 1203128 A1 | 10/2015 |
| IL | 233651 | 8/2014 |
| IL | 233896 | 9/2014 |
| IL | 230930 A | 6/2017 |
| IL | 233851 A | 6/2019 |
| IL | 233653 A | 4/2020 |
| IL | 233885 A | 5/2020 |
| IL | 233894 A | 5/2020 |
| IL | 233895 A | 5/2020 |
| JP | S4991583 U | 8/1974 |
| JP | S5736898 U | 2/1982 |
| JP | S6033891 U | 3/1985 |
| JP | S60127794 U | 8/1985 |
| JP | H022331 A | 1/1990 |
| JP | 2006503572 A | 2/2006 |
| JP | 2010506594 A | 3/2010 |
| JP | 2010536336 A | 12/2010 |
| JP | 2012507287 A | 3/2012 |
| JP | 2014524313 A | 9/2014 |
| JP | 2014532433 A | 12/2014 |
| JP | 2015503335 A | 2/2015 |
| JP | 2015505474 A | 2/2015 |
| JP | 2015505475 A | 2/2015 |
| JP | 2015505476 A | 2/2015 |
| JP | 2015506182 A | 3/2015 |
| JP | 2015508641 A | 3/2015 |
| JP | 2015512617 A | 4/2015 |
| JP | 2015513393 A | 5/2015 |
| JP | 2015518730 A | 7/2015 |
| JP | 2015523089 A | 8/2015 |
| JP | 2015536154 A | 12/2015 |
| JP | 2016509852 A | 4/2016 |
| JP | 2016510994 A | 4/2016 |
| JP | 2016517701 A | 6/2016 |
| JP | 2016523565 A | 8/2016 |
| JP | 2018166509 A | 11/2018 |
| KR | 20140070543 A | 6/2014 |
| KR | 20140090138 A | 7/2014 |
| KR | 20140125822 A | 10/2014 |
| KR | 20140125827 A | 10/2014 |
| KR | 20140125828 A | 10/2014 |
| KR | 20140125829 A | 10/2014 |
| KR | 20140127288 A | 11/2014 |
| KR | 20150003845 A | 1/2015 |
| KR | 20150005514 A | 1/2015 |
| KR | 20150035488 A | 4/2015 |
| MA | 20150054 A1 | 2/2015 |
| MA | 20150055 A1 | 2/2015 |
| MA | 20150056 A1 | 2/2015 |
| MA | 20150057 A1 | 2/2015 |
| MA | 20150058 A1 | 2/2015 |
| MA | 20150153 A1 | 5/2015 |
| MA | 20150169 A1 | 6/2015 |
| MX | 2014009396 A | 2/2015 |
| MX | 2014009398 A | 2/2015 |
| MX | 2014009393 A | 5/2015 |
| MX | 2014009394 A | 5/2015 |
| MX | 2014009397 A | 5/2015 |
| NZ | 627439 A | 9/2015 |
| NZ | 628058 A | 1/2016 |
| RU | 157882 U1 | 12/2015 |
| RU | 2581999 C2 | 4/2016 |
| SG | 2014013627 A | 7/2014 |
| TW | 201315397 A | 4/2013 |
| WO | WO-2010045671 A1 | 4/2010 |
| WO | WO-2012156695 A1 | 11/2012 |
| WO | WO-2013020280 A1 | 2/2013 |
| WO | WO-2013025921 A1 | 2/2013 |
| WO | WO-2013068081 A1 | 5/2013 |
| WO | WO-2013068100 A1 | 5/2013 |
| WO | WO-2013098405 A2 | 7/2013 |
| WO | WO-2013116558 A1 | 8/2013 |
| WO | WO-2013116561 A1 | 8/2013 |
| WO | WO-2013116565 A1 | 8/2013 |
| WO | WO-2013116567 A1 | 8/2013 |
| WO | WO-2013116568 A2 | 8/2013 |
| WO | WO-2013116571 A1 | 8/2013 |
| WO | WO-2013116572 A1 | 8/2013 |
| WO | WO-2013120566 A2 | 8/2013 |
| WO | WO-2013121608 A1 | 8/2013 |
| WO | WO-2013138384 A2 | 9/2013 |
| WO | WO-2013138384 A3 | 10/2013 |
| WO | WO 2013156339 | 10/2013 |
| WO | WO-2013179524 A1 | 12/2013 |
| WO | WO-2014116974 A1 | 7/2014 |
| WO | WO-2014140273 A2 | 9/2014 |
| WO | WO-2014158051 A1 | 10/2014 |
| WO | WO-2014159250 A1 * 10/2014 ............... A24D 3/17 |
| WO | WO-2013116568 A3 | 11/2014 |
| WO | WO-2014184239 A1 | 11/2014 |
| WO | WO-2015013108 A2 | 1/2015 |
| WO | WO-2015013108 A3 | 4/2015 |
| WO | WO-2015047954 A1 | 4/2015 |
| WO | WO-2015128665 A1 | 9/2015 |
| WO | WO-2015128666 A1 | 9/2015 |
| WO | WO-2015128667 A1 | 9/2015 |
| WO | WO-2016024083 A1 | 2/2016 |
| WO | WO 2016076178 | 5/2016 |
| WO | WO-2016084120 A1 | 6/2016 |
| WO | WO-2016135342 A2 | 9/2016 |
| WO | WO-2017149152 A1 | 9/2017 |
| WO | WO-2017160559 A1 | 9/2017 |

OTHER PUBLICATIONS

Application and File History for U.S. Appl. No. 16/333,570, filed Mar. 24, 2019, Inventor: Hepworth et al.

(56) References Cited

OTHER PUBLICATIONS

Application and File History for U.S. Appl. No. 16/333,568, filed Mar. 24, 2019, Inventor: Hepworth et al.
U.S. Appl. No. 16/333,563, filed Mar. 14, 2019, inventors Hepworth, et al.
Communication pursuant to Article 94(3) EPC for Application No. 1778008.3, dated Sep. 11, 2020, 8 pages.
International Preliminary Report on Patentability for Application No. PCT/EP2017/073057, dated Mar. 28, 2019, 9 pages.
International Preliminary Report on Patentability for Application No. PCT/EP2017/072811, dated Aug. 20, 2018, 7 pages.
International Preliminary Report on Patentability for Application No. PCT/EP2017/072814, dated Nov. 30, 2018, 8 pages.
International Preliminary Report on Patentability for Application No. PCT/EP2017/072813, dated Nov. 30, 2018, 9 pages.
International Preliminary Report on Patentability for Application No. PCT/EP2017/073061, dated Mar. 28, 2019, 7 pages.
International Search Report and Written Opinion for Application No. PCT/EP2017/072811, dated Dec. 11, 2017, 15 pages.
International Search Report and Written Opinion for Application No. PCT/EP2017/072813, dated Dec. 11, 2017, 12 pages.
International Search Report and Written Opinion for Application No. PCT/EP2017/073057, dated Feb. 7, 2018, 16 pages.
International Search Report and Written Opinion for Application No. PCT/EP2017/073061, dated Jan. 8, 2018, 13 pages.
Korean Office Action dated Oct. 26, 2020 for Korean Application No. 10-2019-7010642 27 pages.
Korean Office Action dated Oct. 26, 2020 for Korean Application No. 10-2019-7010644, 21 pages.
Notice of Reasons for Rejection for Japanese Application No. 2019-535975, dated Jul. 7, 2020, 9 pages.
Office Action for Korean Application No. 10-2019-7010649, dated Jan. 19, 2021, 7 pages.
Office Action dated Feb. 2, 2021 for Japanese Application No. JP2019-513828, 7 pages.
Office Action dated Aug. 20, 2020 for Russian Application No. 2019107330, 13 pages.
Office Action dated Jul. 21, 2020 for European Application No. 17780009.1, 7 pages.
Office Action dated Jul. 21, 2020 for Japanese Application No. 2019-513761, 11 pages.
Office Action dated Jul. 21, 2020 for Japanese Application No. 2019-513827, 9 pages.
Office Action dated Jul. 21, 2020 for Japanese Application No. 2019-513842, 11 pages.
Office Action dated Jul. 7, 2020 for Japanese Application No. JP2019-513828, 12 pages.
Search Report dated Mar. 2, 2018 for Great Britain Application No. GB1615609.3, 4 pages.
Office Action for Japanese Application No. 2019-535975, dated Oct. 19, 2021, 4 pages.
Notice of Reasons for Refusal for Japanese Application No. 2019-535975, dated Apr. 12, 2022, 18 pages.

\* cited by examiner

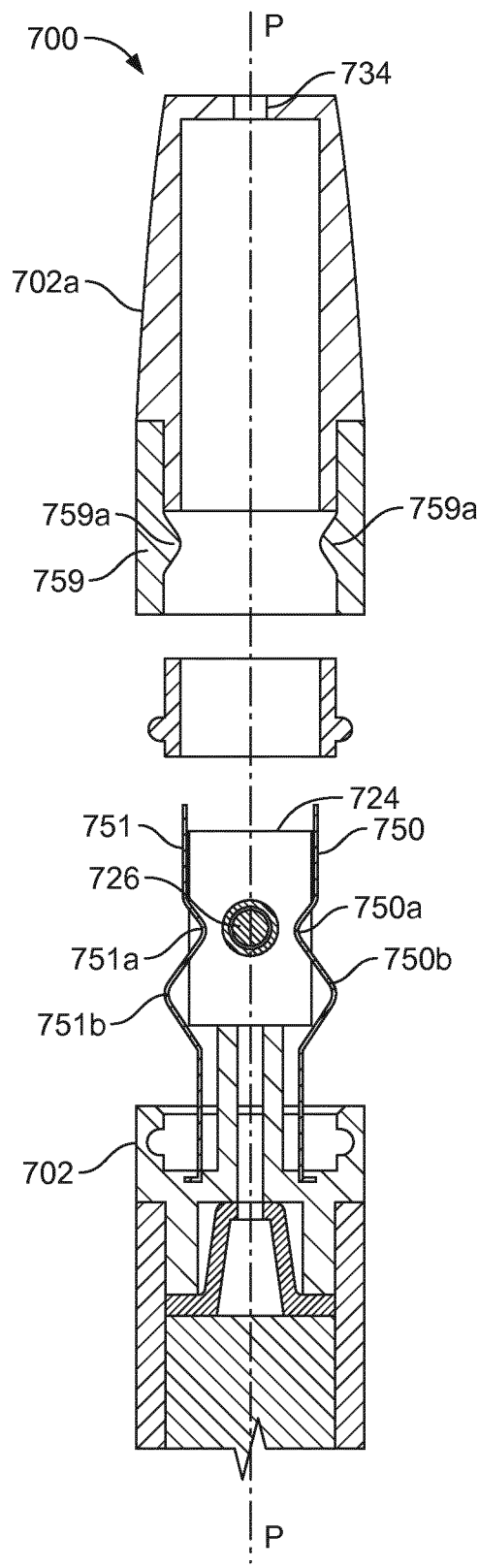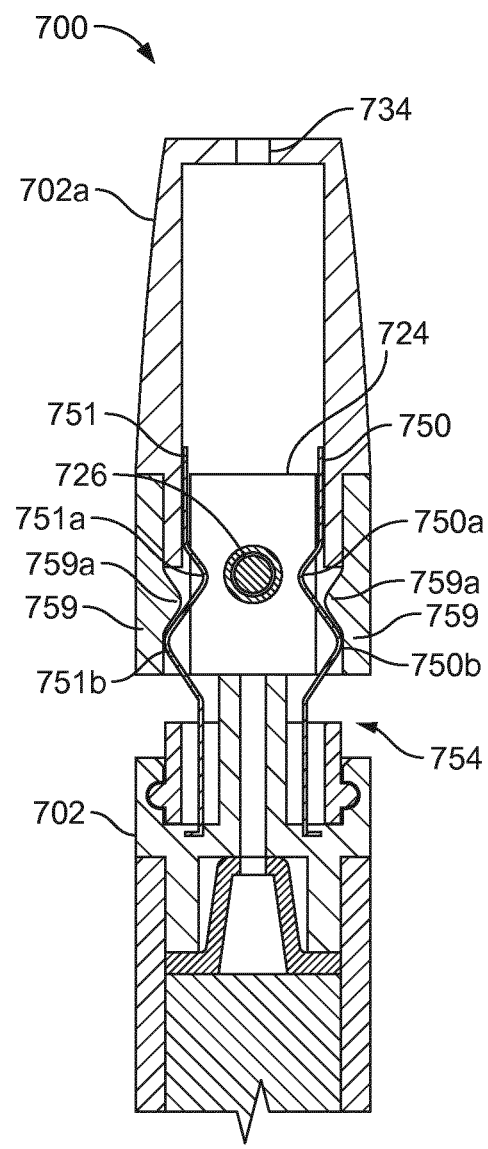
FIG. 7a
FIG. 7b

RECEPTACLE SECTION

PRIORITY CLAIM

The present application is a National Phase entry of PCT Application No. PCT/EP2017/072814, filed Sep. 12, 2017, which claims priority from GB Patent Application No. 1615603.6, filed Sep. 14, 2016, which is hereby fully incorporated herein by reference.

TECHNICAL FIELD

The present disclosure relates to a receptacle section, and more particularly to a receptacle section for an aerosol provision article.

BACKGROUND

Smoking articles such as cigarettes, cigars and the like burn tobacco during use to create tobacco smoke. Attempts have been made to provide alternatives to these articles that burn tobacco by creating products that release compounds without burning.

Examples of such products are heating devices which release compounds by heating, but not burning, the material. The material may be for example tobacco or other non-tobacco products, which may or may not contain nicotine. As another example, there are aerosol provision articles such as so-called e-cigarette devices. These devices typically contain a liquid which is heated to vaporize the liquid to produce an inhalable vapor or aerosol. The liquid may contain nicotine and/or flavorings and/or aerosol-generating substances, such as glycerol. The known e-cigarette devices typically do not contain flavorings other than those in the liquid.

SUMMARY

According to a first aspect of the present disclosure, there is provided a receptacle section for an aerosol provision article, the aerosol provision article for generating a flow of aerosol in use, the receptacle section arranged for receiving therein an activatable element for modifying, once activated, a property of said flow of aerosol, the receptacle section comprising at least one activating element operable to apply, after an installation of said activatable element in the receptacle section by a user, a force to said activatable element to activate said activatable element installed in the receptacle section in use.

The at least one breaking element may be moveable between a first position and a different, second position for activating said activatable element installed in the receptacle section in use, and movement of the at least one breaking element from the first position to the second position may cause said force to be applied to activate said activatable flavor element installed in the receptacle section in use.

The first position may be for allowing installation of said activatable element in the receptacle section by a user.

The movement may comprise movement of the at least one activating element along an axis substantially perpendicular to a longitudinal axis of the receptacle section.

The receptacle section may define a channel for having said activatable element installed therein, and the at least one activating element may be slidably mounted through a side wall of the receptacle section and may be operable by a user to slide between the first position and the second portion, and in the second position the at least one activating element may extend into the channel thereby to apply said force to activate said activatable element received in the channel in use.

The receptacle section may comprise at least one reshaping element extending along at least a portion of the channel, and the reshaping element may be moveable in a direction substantially perpendicular to the longitudinal axis of the receptacle section and biased towards the channel, thereby allowing reshaping of said activatable element received in the channel after a deformation due to said activation of said activatable element in use.

The at least one reshaping element may be oriented at or near a right angle about the longitudinal axis of the receptacle section with respect to one of the at least one activating element.

The receptacle section may comprise at least two said activating elements, and at least two said reshaping elements, and a first said activating element may be located on an opposite side of the channel to a second said activating element, and a first said reshaping element may be located on an opposite side of the channel to a second said reshaping element.

The receptacle section may define a channel for having said activatable element installed therein, and the at least one activating element may comprise a resilient member extending along at least a portion of the channel, and the resilient member may be operable to bend between the first position and the second position, and in the second position at least a portion of the resilient member may protrude into the channel, thereby to apply said force to activate said activatable element received in the channel in use.

An end of the at least one resilient member may be free to move relative to the receptacle section.

The resilient member may comprise an inwardly protruding portion protruding from the resilient member towards the channel, the inwardly protruding portion being for contacting said activatable element received in the channel in use, thereby to apply said force to activate said activatable element received in the channel in use.

The resilient member may comprise an outwardly protruding portion, the outward protruding portion protruding out from the resilient member away from the channel, and being for contacting an operation element of the receptacle section.

The receptacle section may comprise a housing in which the at least one resilient member and said activatable element is housed, and the operation element may be slidably mounted to the housing thereby allowing sliding movement of the operation element relative to the housing substantially parallel to a longitudinal axis of the receptacle section, and the operation element may be operable by a user to slide between a first operation element position in which the operation element is positioned relatively away from the outward protruding portion of the resilient member, and a second operation element position in which the operation element is positioned relatively towards the outward protruding portion of the resilient member, and sliding of the operation element from the first operation element position to the second operation element position may cause bending of the resilient member from the first position to the second position, thereby applying said force to activate said activatable element received in the channel in use.

The operation element may comprise an inwardly protruding portion protruding out of the operation element towards the resilient member, and when the operation element is in the second operation element position, the inward protruding portion of the operation element may be longitudinally aligned with the outward protruding portion of the resilient member.

The receptacle section may comprise a housing in which the at least one resilient member is housed and said activatable element is housable, and the receptacle section may comprise an operation element, and the operation element may be rotatably mounted to the housing thereby allowing rotation of the operation element relative to the housing about the longitudinal axis of the receptacle section, and the operation element may define a first inner radial dimension and a second, smaller inner radial dimension, and the operation element may be operable by a user to rotate between a first operation element orientation in which the first inner radial dimension is rotationally aligned with the resilient member, and a second operation element orientation in which the second inner radial dimension is rotationally aligned with the resilient member, and rotation of the operation element from the first operation element orientation to the second operation element orientation may cause said bending of the resilient member from the first position to the second position, thereby applying said force to activate said activatable element received in the channel in use.

The inner radial dimension of the operation element may vary gradually from the first inner radial dimension to the second inner radial dimension.

The receptacle section may comprise a resilient outer portion, wherein the resilient outer portion is connected to the resilient member to bias the resilient member to the first position.

The receptacle section may comprise at least two said resilient members, and a first said resilient member may be located on an opposite side of the channel to a second said resilient member.

The activatable element may be installed in the receptacle section.

The activatable element may comprise a substance for modifying said property of the aerosol, and said force may cause the substance to be exposed, thereby to modify said property of said flow of aerosol.

The activatable element may comprise a breakable capsule in which the substance is contained, and said force may break the capsule thereby to expose the substance.

The breakable capsule may be held in a carrier material, and the substance may be a liquid and/or gel, and said force may break the breakable capsule to release the liquid and/or gel into the carrier material.

Said property may be one or more of an organoleptic property of the aerosol, a flavor of the aerosol, and the pH of the aerosol.

The receptacle section may comprise a connecting portion for releasably connecting the receptacle section to said aerosol provision article.

According to a second aspect of the present disclosure, there is provided a mouthpiece for an aerosol provision article, said aerosol provision article being for generating a flow of aerosol in use, the mouthpiece comprising the receptacle section according to the first aspect.

According to a third aspect of the present disclosure, there is provided an aerosol provision article for generating a flow of aerosol in use, the aerosol provision article comprising the receptacle section according to the first aspect, and/or the mouthpiece according to the second aspect.

The aerosol provision article may comprise: a container for holding a liquid or a material; a heater for volatilizing liquid held in the container to generate said flow of aerosol in use or for heating but not combusting the material to generate said flow of aerosol in use.

Further features and advantages of the disclosure will become apparent from the following description of embodiments of the disclosure, given by way of example only, which is made with reference to the accompanying drawings.

BRIEF DESCRIPTION OF THE DRAWINGS

FIG. 1 shows a schematic cross section of an aerosol provision article according to an example.

FIG. 2 shows a schematic perspective view of a part of an aerosol provision article comprising a first receptacle section according to a first example. FIGS. 3*a* and 3*b* show schematic cross sections of a part of an aerosol provision article comprising a second receptacle section in different configurations according to a second example.

FIGS. 4*a* to 4*c* show schematic cross sections of part of an aerosol provision article comprising a third receptacle section in different configurations according to a third example.

FIGS. 5*a* to 5*d* show schematic cross sections of part of an aerosol provision article comprising a fourth receptacle section in different configurations according to a fourth example.

FIGS. 6*a* to 6*c* show schematic cross sections of part of an aerosol provision article comprising a fifth receptacle section in different configurations according to a fifth example.

FIGS. 7*a* to 7*d* show schematic cross sections of part of an aerosol provision article comprising a sixth receptacle section in different configurations according to a sixth example.

FIGS. 8*a*, 8*b*, and 8*d* show schematic cross sections of part of an aerosol provision article comprising a seventh receptacle section in different configurations according to a seventh example.

FIGS. 8*c* and 8*e* show schematic cross sections of the example receptacle section shown in FIGS. 8*a* and 8*d* respectively, but in a plane perpendicular to the plane of the cross sections shown in FIGS. 8*a* and 8*d*, respectively.

DETAILED DESCRIPTION

Referring to FIG. 1, a schematic of an example aerosol provision article 100 is illustrated. The aerosol provision article 100 is an inhalation device (i.e. a user uses it to inhale an aerosol provided by the device). The aerosol provision article is hand-held. In this example, the article 100 is an electronic cigarette device 100. In broad outline, the device 100 volatilizes a liquid to form a vapor or an aerosol which passes through an activatable element 124 received in a receptacle section 102 of the device 100. In this example the receptacle section 102 is a mouthpiece of the device 102. The activatable element 124, once activated, modifies a property of the vapor or aerosol passing through the mouthpiece 102 for inhalation by a user. For example, the activatable element 124 may be a breakable flavor element 124 which, once broken, imparts a flavor to the vapor or aerosol passing through the mouthpiece 102 for inhalation by a user.

In this respect, first it may be noted that, in general, a vapor is a substance in the gas phase at a temperature lower than its critical temperature, which means that for example the vapor can be condensed to a liquid by increasing its pressure without reducing the temperature. On the other hand, in general, an aerosol is a colloid of fine solid particles or liquid droplets, in air or another gas. A colloid is a substance in which microscopically dispersed insoluble particles are suspended throughout another substance.

Returning to FIG. 1, the device 100 comprises an outer body 106 housing a liquid container 122 containing liquid 116, an atomizer 108, and a battery portion 112. The atomizer 108 is (electrically) connected to the battery portion 112.

The mouthpiece 102, in this example, is removably connected to the outer body 106. The mouthpiece 102 may be removed from the outer body 106, for example to allow access to the liquid container 122, for example to refill the liquid 116 held in the liquid container 122. The mouthpiece 102 has a channel 132 running there through that defines a flow path for a flow of vapor or aerosol. The mouthpiece 102 has removably received in the channel 132 a breakable flavor element 124 for imparting, once broken, a flavor to said flow of aerosol or vapor that passes through the mouthpiece 102 in use.

The breakable flavor element 124 may comprise flavored materials that, once the breakable flavor element is broken (e.g. crushed, pierced mechanically activated), may be used to create a desired taste or aroma, or other properties, such as nicotine content. In this example, the breakable flavor element 124 comprises a breakable flavor capsule 126 for releasing, when broken for example by a user, a flavorant such as a liquid and/or a gel for imparting a flavor to a flow of at least one of a vapor and an aerosol. In this example, the breakable flavor element 124 comprises a breakable flavor capsule 126 wrapped or embedded in a carrier material. The carrier material may comprise a material that allows vapor or aerosol to pass there through. The carrier material may comprise a material that holds the liquid and/or gel released from the breakable flavor capsule 126 when it is broken. The carrier material may be any suitable material, for example, cellulose acetate. When the breakable flavor element 124, and hence the flavor capsule 126, is broken (e.g. crushed, pierced, mechanically activated), the flavorant such as a liquid and/or gel contained in the flavor capsule 126 is released into the carrier material so as to flavor vapor or aerosol passing there through.

The breakable flavor element 124 may be porous, for example so as allow vapor or aerosol to pass through it. The breakable flavor element 124 may be self-supporting, so as to be easily handled by a user (for example easily inserted and/or removed from the mouthpiece 102). For example the breakable flavor element 124 may comprise material wrapped partially or wholly in a wrapper, and/or the breakable flavor element 124 may be supported in a resilient housing, for example a plastic housing (not shown). As mentioned above, the breakable flavor element 124 may comprise, for example, a carrier material, such as cellulose acetate or the like. This carrier material may itself be flavored. The breakable flavor element 124 may be cylindrical, and/or comprise a cylindrical portion, so as to fit easily and/or tightly into a corresponding cylindrical channel 132 of the mouthpiece 102.

The device 100 is arranged so that, in use, as the liquid 116 is volatilized so as to produce an aerosol of liquid droplets or sufficiently heated to produce a vapor, at least some or all or substantially all of the aerosol or vapor passes through the breakable flavor element 124 received in the mouthpiece 102 for example so as to entrain constituents of the flavor element 134 therein. In some examples, a vapor is produced that then at least partly condenses to form on aerosol before exiting the device 100.

The liquid container 122 is provided generally centrally of the outer body 106. The liquid container 122 is annular in shape and defines a channel 104 running through the length of the liquid container 122. The liquid container 122 may be formed of rigid, watertight and airtight materials, such as metal, suitable plastics, etc. It will be appreciated that the liquid container 122 may have a different shape, such as conical, frustoconical, or combination of these, etc.

The atomizer 108 is provided with a heater 110 and a wick (not shown) in (thermal) contact with the heater 110. The orientation of the heater 110 is shown schematically and for example the heater 110 may be a coil having its longitudinal axis perpendicular or parallel to the longitudinal axis of the liquid container 108. The wick (not shown) is in contact with the liquid 116. This may be achieved by for example by the wick (not shown) being inserted through a through hole (not shown) in an end wall 122b of the liquid container 122. Alternatively or additionally, the end wall 122b may be a porous member which allows liquid to pass through from the liquid container 122, and the wick (not shown) may be in contact with the porous end wall 122b. The end wall 122b may be for example in the form of a porous ceramic disk. A porous end wall 122b of this type helps to regulate the flow of liquid onto the wick (not shown). The wick (not shown) is generally absorbent and acts to draw in liquid 116 from the liquid container 122 by capillary action (shown in FIG. 1 by arrows A). The wick can be non-woven and may be for example a cotton or wool material or the like, or a synthetic material, including for example polyester, nylon, viscose, polypropylene or the like, or a ceramic material.

The atomizer 108 is (electrically) connected to a battery in the battery portion 116 to enable the heater 110 to be powered. When the heater 110 is powered (which may be instigated for example by the user operating a button (not shown) of the device 100 or by a puff detector (not shown) of the overall device 100, as is known per se, liquid 116 is drawn (shown in FIG. 1 by arrows A) in from the liquid container 122 by the wick and is heated by the heater 110 to volatilize or vaporize the liquid, so as to generate at least one of a vapor and an aerosol.

As the user draws on the mouthpiece 102, air is drawn through an air inlet 118. The liquid 116 is volatized or vaporized by the heater 110 into air from the air inlet 118 thereby to produce a flow of one of a vapor and an aerosol. The flow of vapor or aerosol is drawn through the channel 104 of the liquid container 122, into the channel 132 of the mouthpiece 102, through the flavor element 134 received in the mouthpiece 102, and out from the device 100 for inhalation by a user (shown by arrow B in FIG. 1). The vapor or aerosol picks up (entrains) flavor (and/or other constituents) from the breakable flavor element 124 (for example once the breakable flavor element 124 is broken). One or more constituents of the breakable flavor element 124 is thereby mixed with the flow of at least one of a vapor and an aerosol. In examples where the breakable flavor element 124 contains or includes nicotine, the vapor or aerosol may thereby also contain nicotine entrained from the breakable flavor element 124. A one way valve (not shown) may be provided, for example at or near an upper end 122a of the liquid container 122, so that the vapor or aerosol can only exit the channel 104 and cannot back-flow to the heater 110 or the electronics (not shown) of the device 100.

The breakable flavor element 124 may be or comprise material that may be used to impart a flavor (and/or one or more other constituents) to the aerosol or vapor. In some examples, the one or more constituents of the breakable flavor element 124 may comprise constituents inherent to the material itself. The material may for example consist of or comprise tobacco. As the aerosol or vapor passes through and over the tobacco, the aerosol or vapor entrains organic and other compounds or constituents from the tobacco that lend tobacco its organoleptic properties, thus imparting the flavor to the aerosol or vapor. It will be understood however that materials other than tobacco may be used to impart different flavors (and/or one or more other constituents) to the aerosol or vapor flow. The flavor element 124 may comprise constituents added to a material of the flavor element 124.

Nicotine may be provided in the liquid 116. Accordingly, where it is intended that the device 100 provides nicotine for the user, the nicotine may be provided in the liquid 116, may be obtained from the flavor element 124, or any combination of these. Likewise, flavorings may be added to the flavor element 124 (whether or not the flavor element 124 is or includes tobacco) and/or to the liquid 116. A material of the flavor element 124 may be a solid material, or be a mixture of solid materials, one or more of each comprising one or more constituents that can be mixed with the flow of vapor or aerosol. It will be appreciated that the flavor element 124 may comprise one or more other constituents that are not entrained into the aerosol or vapor passing there through. It will also be appreciated that the flavor element 124 may comprise a portion that does not impart any flavor and/or release any constituents into the flow of a vapor or an aerosol.

Various receptacle sections for use with an aerosol provision article (e.g. device 100 in FIG. 1) will now be described. In broad overview, the various receptacle sections are arranged for receiving therein a breakable flavor element for releasing, once broken, a flavorant for imparting flavor to a flow of at least one of a vapor and an aerosol generated by an overall aerosol provision article in use. For example, the flavor may be imparted by the flow of at least one of an aerosol or vapor passing through the breakable flavor element installed in the receptacle section in use. The various receptacle sections each comprise at least one breaking element operable to break, after an installation of the breakable flavor element in the receptacle section by a user, the breakable flavor element installed in the receptacle section in use. The various receptacle sections therefore provide a convenient way for a user to break a breakable flavor element after the breakable flavor element has been installed in an overall aerosol provision article (e.g. device 100 in FIG. 1) with which the receptacle section is being used. This allows, for example, a user to quickly and easily control, for example during use, whether the vapor or aerosol for inhalation is not flavored by a flavor of the breakable flavor element (i.e. when the breakable flavor element is in a non-broken state), or whether the vapor or aerosol for inhalation is flavored by a flavor of the breakable flavor element (i.e. when the breakable flavor element is in a broken (activated) state).

For reasons of convenience, as used herein the term aerosol should be taken as encompassing an aerosol, a vapor or a mixture of an aerosol and vapor.

Figure 2:
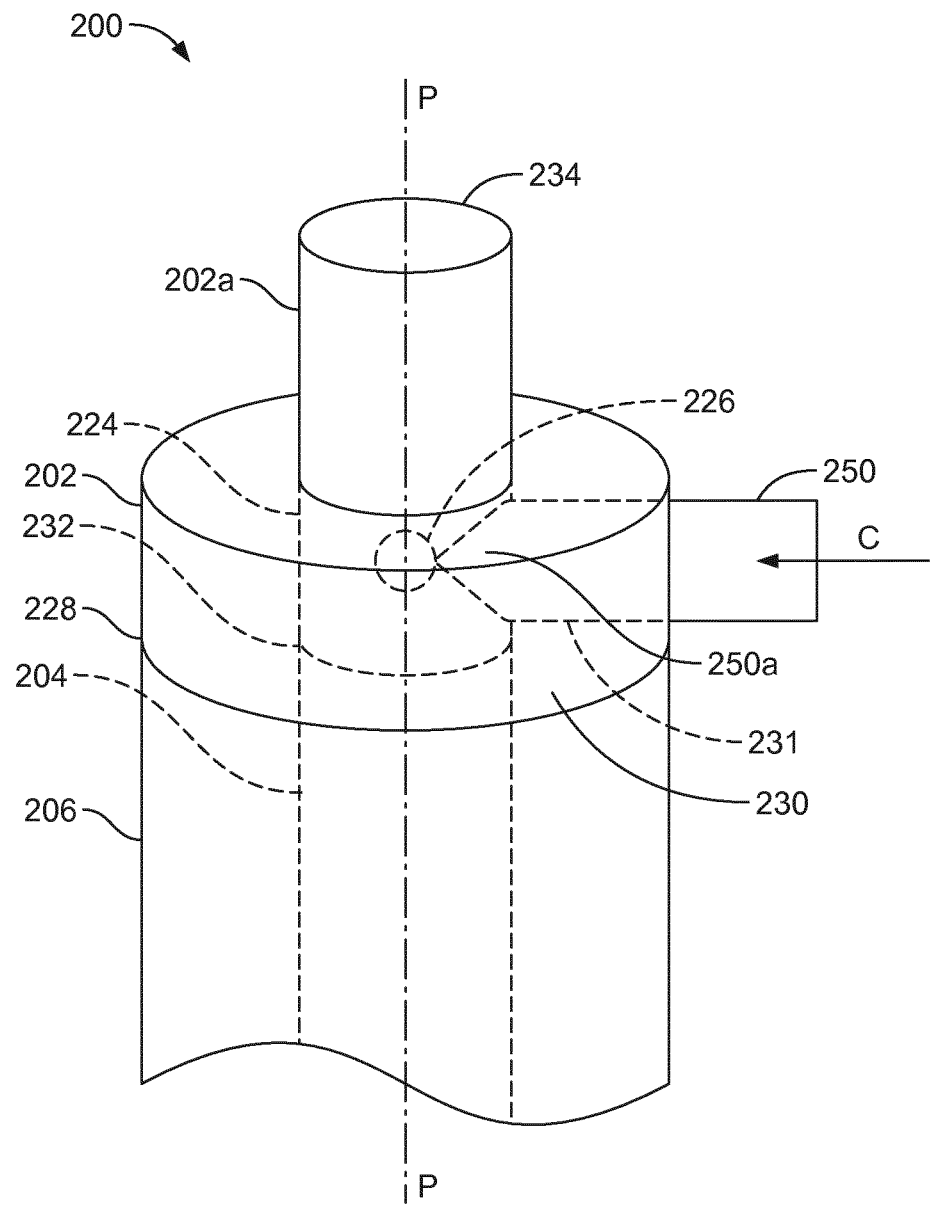

Turning first to FIG. 2, there is illustrated schematically a perspective view of a part of a device 200 that comprises an example receptacle section 202. In this example, the receptacle section 202 is a mouth-end section 202 of the device 200, that is, the receptacle section 202 is located toward an end of the device 200 for receipt into a user's mouth in use. In some examples, the mouth-end section 202, or at least a portion thereof, is a mouthpiece 202. In other examples, the receptacle section 202 may at a different location in the overall device 200, for example intermediate of the body and the mouthpiece. For brevity, features in FIG. 2 and the functioning thereof that are the same or similar to those features already described with reference to FIG. 1 are given similar reference numerals to as in FIG. 1 but increased by 100, and will not be described in detail again.

The mouth-end section 202 is generally cylindrical in shape. The mouth-end section 202 is removably connected to a body 206 of the overall device 200, via a connecting means 228. The connecting means 228 may be, for example, a threaded connection or the like, for example the mouth-end section 202 may have a male thread connectable to a corresponding female thread of the body 206. The mouth-end section 202 comprises a removable mouth portion 202a for receipt into a user's mouth (not shown). The mouth-end section 202 defines a channel 232 internal thereof. The channel 232 extends from an opening (not shown in FIG. 2) for fluid connection with an aerosol flow path 204 of the overall device (e.g. device 100 of FIG. 1) to an opening 234 of the mouth portion 202a for outlet of aerosol for inhalation by a user. A breakable flavor element 224, comprising a breakable flavor capsule 226, is received in the channel 232.

The mouth-end section comprises a breaking element 250. In this example, only one breaking element 250 is shown in FIG. 2, but it will be appreciated that more than one breaking elements may be used, for example, any number of breaking elements. The breaking element 250 is moveable between a first position (as illustrated in FIG. 2) and a second position. The first position is for allowing installation of the breakable flavor element 224 in the mouth-end section 202 by a user. For example, when the breaking element 250 is in the first position (as illustrated in FIG. 2), the breaking element 250 does not extend into the channel 232, and hence the channel 232 is clear for installation of a breakable flavor element 234 therein, for example via the opening 234 of the mouth portion 202a. The second position (not shown) is for breaking the flavor element 234 installed in the mouth-end section 202 in use. Movement (arrow C) of the breaking element 250 from the first position to the second position breaks the breakable flavor element 234 installed in the mouth-end section 202 in use.

Specifically, the movement of the breaking element 250 comprises movement of the breaking element 250 along an axis substantially perpendicular to a longitudinal axis P-P of the mouth-end section 202. In this example, the breaking element 250 is an elongate rod. The mouth-end section 202 defines an opening 231 in a side wall 230 of the mouth-end section 202 that extends from an outer surface of the mouth-end section 202 to the channel 232 defined by the mouth-end section 202. The breaking element 250 is received in the opening 231 of the side wall 230, and thereby slidably mounted through the side wall 230 of the mouth-end section 202. The breaking element 250 is longer than the side wall 230 is thick, and hence in the first position (as shown in FIG. 2) protrudes out of the opening 231 away from the channel 232. The breaking element 250 is operable by a user to slide (arrow C) between the first position (as shown in FIG. 2) and the second position (not shown), i.e. to slide through the side wall 230 and into the channel 232. In the second position the breaking element 250 extends into the channel 232 thereby to break the breakable flavor element 224 received in the channel 232 in use. The breaking element 250 breaks the breakable flavor element 250 laterally.

The breaking element 250 narrows at one end 250a for breaking the breakable flavor element 224. The narrowing at the end 250a of the breaking element 250 increases the pressure exerted on the breakable flavor element 224 by the breaking element 250 for a given force applied by a user. This increases the ease with which a user may break the breakable flavor element 224.

In use, for example when the mouth-end section 202 is connected to the rest of the device (e.g. as shown schematically for device 100 in FIG. 1), a user may install a breakable flavor element 224 into the mouth-end section 202. At some later time, user may then operate the breaking element 250 to break the breakable flavor element 224. When a user draws on the mouth-end section 202, air is drawn in through an air inlet (120 in FIG. 1), and a heater (110 in FIG. 1) volatizes liquid (116 in FIG. 1) held in the liquid container (122 in FIG. 1) into the inlet air to generate a flow of aerosol. The flow passes through the channel (104 in FIG. 1) in the liquid container (122 in FIG. 1), into the channel 232 of the mouth-end section 202, through the (broken) breakable flavor element 234, and exits from the outlet 234 of the mouth portion 202a for inhalation by the user. The flow of aerosol through the (broken) breakable flavor element 234 thereby entrains one or more of the constituents released by the broken flavor element 234 in the flow. This use description is applicable also to the other examples described herein, and so will not be described in detail again.

Figure 3A:
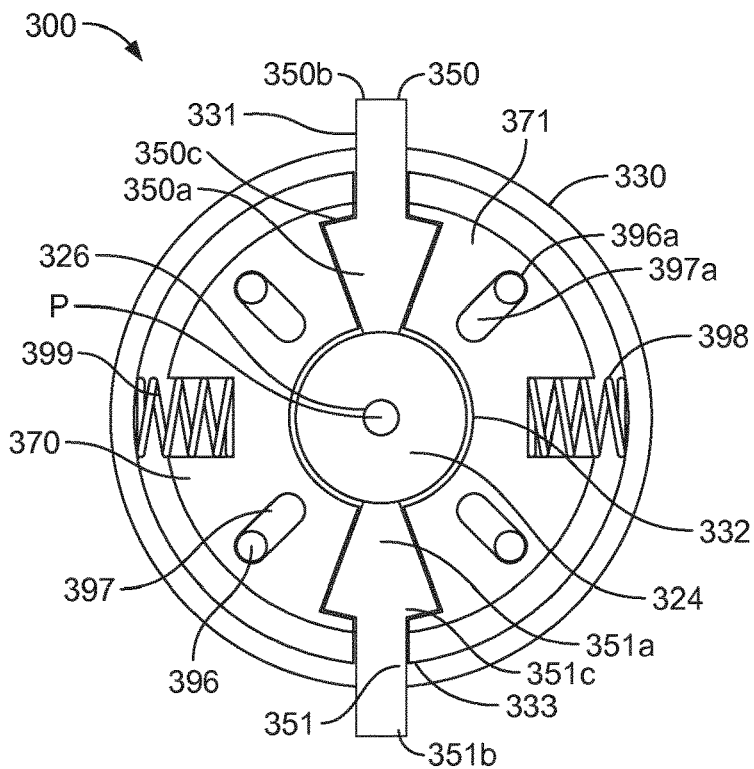
Figure 3B:
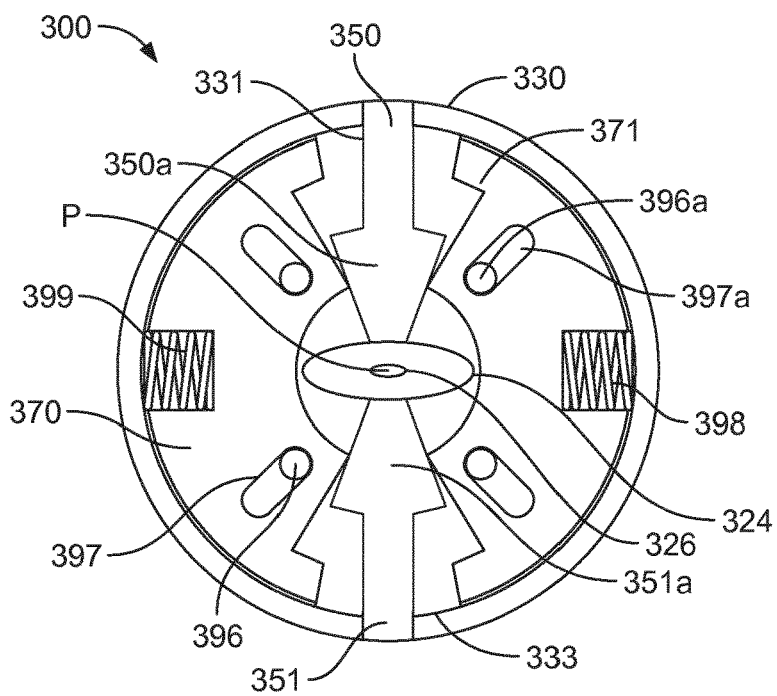

Referring now to FIGS. 3a and 3b, there is illustrated schematically cross sections of another part of an aerosol provision device 300 comprising an example receptacle section 302 in different configurations. The cross sections in FIGS. 3a and 3b are taken in a plane perpendicular to the longitudinal axis P of the receptacle section 302. In this example, the receptacle section 302 is again a mouth-end section 302. For brevity, features in FIG. 3 and the functioning thereof that are the same or similar to those features already described with reference to FIG. 2 are given similar reference numerals to as in FIG. 2 but increased by 100, and will not be described in detail again.

The mouth-end section 302 illustrated in FIGS. 3a to 3c is similar to the mouth-end section 202 illustrated in FIG. 2. A breakable flavor element 324 comprising a breakable flavor capsule 326 is received in a channel 322 of the mouth-end section 302. A first breaking element 350 that narrows at one end 350a is received through an opening 331 in a side wall 330 of the mouth-end section 302, and is thereby operable between first and second positions as described above with respect to the breaking element 250 described above with reference to FIG. 2.

However, the mouth-end section 302 illustrated in FIGS. 3a to 3c comprises a second breaking element 351. The second breaking element 351 is essentially the same as the first breaking element 350. The second breaking element 351 is an elongate rod that narrows at one end 351a, and is received through a second opening 333 in the side wall 330 of the mouth-end section 302 thereby to be slidably mounted through the side wall 330 of the mouth-end section 302. Similarly to the first breaking element 350, the second breaking element 351 is operable by a user to slide between a first position (as in FIG. 3a) in which the breaking element 351 does not extend into the channel 332, and a second position (as in FIG. 3b) in which it does.

In this example, both the first breaking element 350 and the second breaking element 351 are arrow like in cross section. Respective ends 350a, 351a take the form of an arrow head on the end of a main rod like body 350b, 351b. The breaking elements 350, 351 therefore each comprise a respective step 350c, 351c in width between the respective ends 350a, 351a and respective bodies 350b, 351b. The respective bodies 350b, 351b are received through the respective openings 331, 333. The width of the respective ends 350a, 351a at the respective steps 350c, 351c, being larger than that of the respective openings 331, 333, prevents the respective breaking elements 350, 351 from being removed entirely radially outwardly through the respective openings 331, 333.

The second opening 333 and the second breaking element 351 are located on an opposite side of the channel 332 to the first opening 331 and the first breaking element 350. The second opening 333 and the second breaking element 351 are located at the same position along the longitudinal axis P-P of the mouth-end section 302 to the first opening 331 and the first breaking element 350. The first breaking element 350 and the second breaking element 351 are thereby operable by a user to slide towards each other along an axis substantially perpendicular to a longitudinal axis P-P of the mouth-end section 302. A breakable flavor element 324 received in the channel 332 of the mouth-end section 302 may therefore be broken between the narrow ends 350a, 351a of the first breaking element 350 and the second breaking element 351 respectively. There being two operable breaking elements 350, 351 reduces the force required per breaking element 350, 351 to break the breakable flavor element 224 in the channel 332 there between. The two breaking elements 350, 351 being opposing allows for convenient manual operation of the breaking elements 350, 351, for example using a thumb and an index finger of a user's hand, respectively.

The mouth-end section 302 illustrated in FIGS. 3a and 3b comprises a first reshaping element 370 and a second reshaping element 371 each extending along a portion of the channel 332 on opposite sides of the channel 332. The reshaping elements 370, 371 are internal of the side wall 330 of the mouth-end section 302. The reshaping elements 370, 371 are moveable in a direction substantially perpendicular to the longitudinal axis P-P of the mouth-end section 302. Specifically, the first reshaping element 370 comprises at least one elongate slot 397 for receiving a pin 396 of the mouth-end section 302. Similarly, the second reshaping element 371 comprises at least one elongate slot 397a for receiving a pin 396a of the mouth-end section 302. The elongate slots 397, 397a extend radially of the longitudinal axis P-P of the mouth-end section 302, hence allowing sliding movement of the respective reshaping elements 370, 371 relative to the mouth-end section 302 in a direction substantially perpendicular to the longitudinal axis P-P of the mouth-end section 302. The reshaping elements 370, 371 are oriented substantially at right angles about the longitudinal axis P-P relative to the breaking elements 350, 351. Movement of the reshaping elements is therefore along an axis substantially at right angles to the axis along which the breaking elements 359, 351 are moveable.

The reshaping elements 370, 371 each contact the breaking elements 350, 351 at their respective narrowing ends 350a, 351a. The reshaping elements 370, 371 are shaped so that a surface of the reshaping element 370, 371 for contacting the breaking element 350, 351 lies in a plane substantially parallel to a plane defined by the narrowing end 350a, 351a of the breaking element 350, 351. When the breaking elements 350, 351 are pushed radially inwardly towards the channel 332, for example so as to break a breakable flavor element 324 received therein, the respective narrowing ends 350a, 351a therefore exert a force on the reshaping elements 370, 371 that causes the reshaping elements 370, 371 to slide radially outwardly away from the channel 332.

The mouth end section 302 comprises a first biasing means 399, for example a spring 399, which biases the first reshaping element 370 away from an inner surface of the side wall 330 and towards the channel 332. Similarly, the mouth end section 302 comprises a second biasing means 398, for example a spring 398, which biases the second reshaping element 371 away from an inner surface of the side wall 330 and towards the channel 332. The reshaping elements 370, 371 may therefore be slid back radially inwardly towards the channel 332, under the force of the respective biasing means 398, 399.

The reshaping elements 370, 371 are oriented at or near right angles about the longitudinal axis P-P of the mouth-end section 302 with respect to the breaking elements 350, 351. When the breaking element 350 breaks (e.g. crushes) the breakable flavor element 324 laterally, the breakable flavor element 324 may deform so at to reduce in width along the breaking axis (i.e. the axis along which the breaking elements 350, 351 slide), and to increase in width along an axis perpendicular to the breaking axis. The reshaping elements 370, 371 being oriented at right angles to the breaking elements 350, 351 allows the reshaping elements 370, 371 to apply, via the biasing means 399, 398, a returning (squeezing) force along an axis substantially perpendicular to the breaking axis. This reduces the width of the breakable flavor element 324 along the axis perpendicular to the breaking axis, and increases the width of the breakable flavor element 324 along the breaking axis, thereby returning the breakable flavor element towards its original shape prior to breaking.

The reshaping elements 370, 371 thereby allow reshaping of the breakable flavor element 324 received in the channel 332 after a deformation of the breakable flavor element 324 due to breaking of the breakable flavor element 324 in use. This reshaping reduces the increase in pressure drop in the breakable flavor element 324 that may result from breaking of the breakable flavor element 324. The reshaping therefore allows for a consistent delivery of aerosol from the overall device 300 whether or not the breakable flavor element 324 has been broken.

Referring now to the sequence shown in FIGS. 3a and 3b, in FIG. 3a, a breakable flavor element is received in the channel 332, and the first breaking element 350 and the second breaking element 351 are each in the first position, i.e. away from the breakable flavor element 324. A user may wish to break the breakable flavor element 324, for example, so as to change a flavor of the aerosol produced by the device 300. A user may therefore push the first breaking element 350 and the second breaking element 351 radially inwards towards each other, i.e. slide the first breaking element 350 and the second breaking element 351 to the second position (FIG. 3b). The breakable flavor element 324 is thereby broken (e.g. crushed) between the first breaking element 350 and the second breaking element 351, and being broken (e.g. crushed), releases a flavor to flavor the aerosol passing there through. In being broken (e.g. crushed), the breakable flavor element 324 is deformed such that its width along an axis perpendicular to the breaking axis increases. The movement of the first breaking element 350 and the second breaking element 351 radially inwards causes the reshaping elements 370, 371 to move radially outwards away from the channel along the axis perpendicular to the breaking axis, hence energizing the biasing means 398, 399. (FIG. 3b). A user may then cease pushing on the breaking elements 350, 351. The biasing means 398, 399 cause the reshaping elements 370, 371 to return radially inwardly to their original positions, and in so doing reshapes the breakable flavor element 324 towards its original form. The movement of the reshaping elements 370, 371 radially inwardly causes the breaking elements to slide radially outwardly to the first position (FIG. 3a).

Although the description of the other example receptacle sections herein does not refer explicitly to a 'reshaping elements' or 'reshaping' of a breakable flavor element, it will be readily appreciated that this feature can be applied equally to the other examples.

Figure 4A:
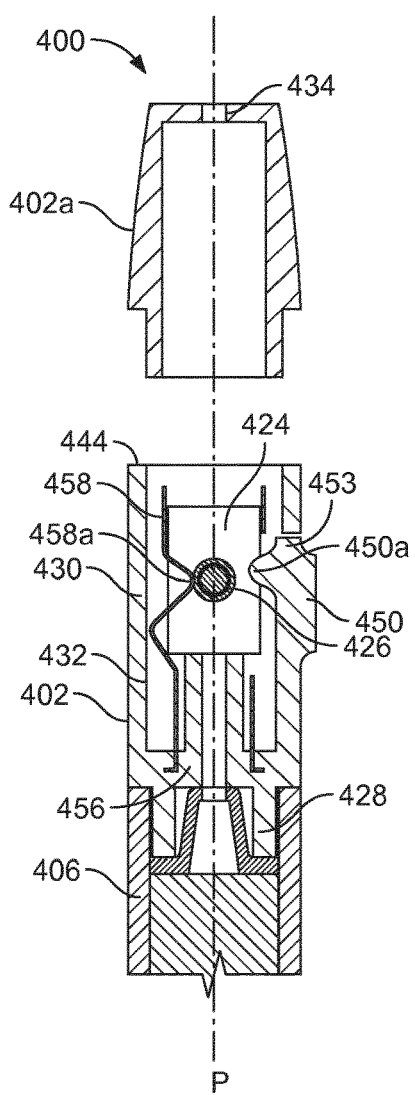
Figure 4B:
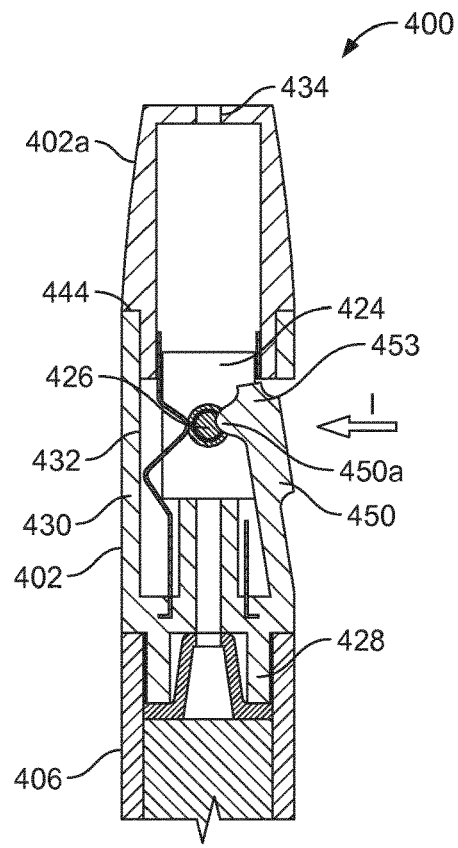
Figure 4C:
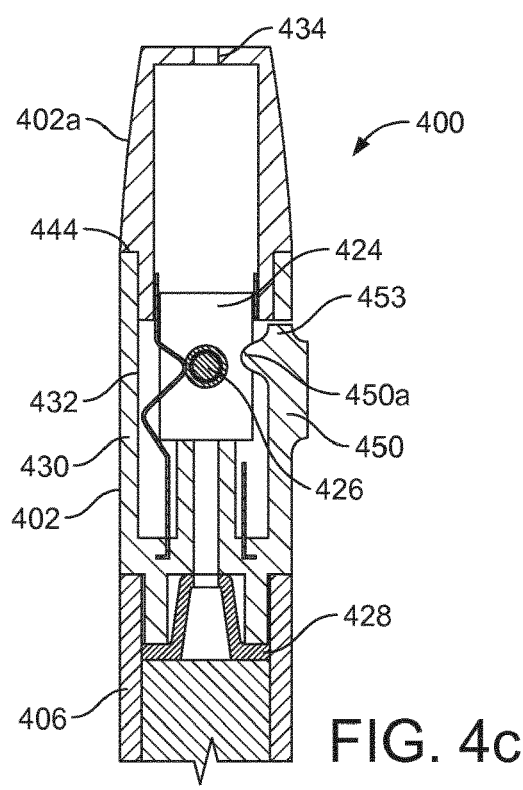

Referring now to FIGS. 4a to 4c, there is illustrated schematically cross section of part of an aerosol provision article 400 with another example receptacle section 402 in different configurations. In this example, the receptacle section 402 is again a mouth-end section 402. For brevity, features in FIG. 4 and the functioning thereof that are the same or similar to those features already described with reference to FIGS. 3a to 3c are given similar reference numerals to as in FIG. 3 but increased by 100, and will not be described in detail again.

As in the mouth-end section 202 illustrated in FIG. 2, the mouth-end section 402 illustrated in FIGS. 4a to 4d defines a channel 432 for having a breakable flavor element 424 comprising a breakable flavor capsule 426 installed therein. The mouth-end section 402 comprises a removable mouth portion 202a defining an outlet 434 for inhalation of aerosol produced by the overall device 400. When the mouth portion 402a is removed, an opening 444 of the channel is exposed, allowing installation of a breakable flavor element 424 therein. The mouth-end section 402 comprises a connecting means 428 for releasably connecting the mouth-end section 402 to a body 406 of the overall device 400. The mouth-end section 402 comprises a breaking element 450 moveable along an axis substantially perpendicular to the longitudinal axis P-P of the mouth-end section 402 between a first position (see FIG. 4a) for allowing installation of the breakable flavor 424 element in the channel 432, and a second position (see FIG. 4b) for breaking said breakable flavor element 424 installed in the channel 432.

However, in this example, the breaking element 450 comprises a resilient member 450 extending along a portion of the channel 432 of the mouth-end section 402, i.e. extending along the channel 432 in a direction substantially parallel to the longitudinal axis P-P of the mouth-end section 402. The resilient member 450 is operable by a user to bend or flex between the first position (see FIG. 4a) and the second position (see FIG. 4b). In the first position (FIG. 4a) the resilient member 450 lies substantially parallel with the channel thereby allowing insertion of a breakable flavor element 424 therein. In the second position (see FIG. 4b) a portion 450a of the resilient member 450 protrudes into the channel 432, thereby to break (e.g. crush) the breakable flavor element 424 received in the channel 432.

In this example, the resilient member 450 forms part of the side wall 430 of the mouth-end section 402 defining the channel 432. One end 453 of the resilient member 450 is free to move relative to the side wall 430. The end 453 of the resilient member 450 is therefore bendable relative to the remainder of the side wall 430 into the channel 432, thereby to break the breakable flavor element 424 received in the channel 432. The breakable flavor element 424 is supported in the channel 432 by a support member 456.

The resilient member 450 comprises, at the end 453 of the resilient member 450 that is free to move, an inward protruding portion 450a protruding from the resilient member 450 towards the channel 432. The inward protruding portion 450a is for contacting the breakable flavor element 424 received in the channel 432, thereby to break said breakable flavor element 424 received in the channel 432 when the resilient member 450 is bent to the second position. The inward protruding portion 450a increases the pressure exerted on the breakable flavor element 424 when the resilient member 450 is bent to the second position for a given lateral force exerted on the resilient member 450 by a user. The inward protruding portion 450a therefore increases the ease with which a user may break the breakable flavor element 424 received in the channel 432. Although this 'inward protruding portion' feature is not explicitly mentioned in every example described herein, it will be appreciated that this feature may be applied equally to those other examples.

The mouth-end section 402 comprises a reacting element 458 extending along a portion of the channel 432 of the mouth-end section 402, i.e. extending along the channel 432 in a direction substantially parallel to the longitudinal axis P-P of the mouth-end section 402. The reacting element 458 is positioned on an opposite side of the channel 432 to the resilient member 450, and hence reacts the force exerted on the breakable flavor element 426 by the resilient member 450 when operated by the user. The breakable flavor element 426 is therefore broken (e.g. crushed) between the resilient member 450 operable by the user and the reacting element 458. Similarly to the resilient member 450, the reacting element 458 comprises an inward protruding portion 458a that protrudes into the channel 432, and which is opposed to the inward protruding portion 450a of the resilient member 450. This (further) increases the pressure exerted on the breakable flavor element 424 when the resilient member 450 is operated by a user, hence (further) increasing the ease with which a user may break a breakable flavor element 424 received in the channel 432.

Referring to the sequence illustrated in FIGS. 4a to 4c, in FIG. 4a, the mouth portion 402a is removed from the mouth-end section 402, thereby to allow an insertion, removal or replacement of the breakable flavor element 424 into the channel 432. A user may replace the mouth portion 402a into the mouth-end section 402. In FIG. 4a, a breakable flavor element 424 is received in the channel 432, and the resilient member 450 is in the first portion, i.e. substantially parallel (unbent) with respect to the longitudinal axis P-P of the mouth-end section 402. At some later stage, a user may wish to break (activate) the breakable flavor element so that aerosol inhaled from the device 400 is flavored there by. A user may therefore push (arrow I) laterally (i.e. in a direction perpendicular to the longitudinal axis P-P of the mouth-end section 402) against the resilient member 450. This causes the resilient member 450 to bend so that the inward protruding portion 450a protrudes into the channel 432 and breaks (activates) the breakable flavor element 424 between the inward protruding portion 450a of the resilient member and the inward protruding portion 458a of the resisting element 458, thereby releasing flavor from the breakable flavor capsule 426. The resilient member 450 is now in the second position (see FIG. 4b). When a user ceases to push on the resilient member 450, due to its resilience (natural springiness), the resilient member 450 returns to the first portion, i.e. returns so as to be substantially parallel (unbent) with respect to the longitudinal axis P-P of the mouth-end section 402.

Referring now to FIGS. 5a to 5d, there is illustrated schematically cross sections of a part of an aerosol provision article 500 with another example receptacle section 502 in different configurations. In this example, the receptacle section is again a mouth-end section 502. For brevity, features in FIGS. 5a to 5d and the functioning thereof that are the same or similar to those features already described with reference to FIGS. 4a to 4c are given similar reference numerals to as in FIGS. 4a to 4d but increased by 100, and will not be described in detail again.

The mouth-end section 502 illustrated in FIGS. 5a to 5d is similar to the mouth-end section 402 illustrated in FIGS. 4a to 4c. A breakable flavor element 524 comprising a breakable flavor capsule 526 is received in a channel 532 of the mouth-end section 502. A first resilient member 550 is bendable along an axis parallel to the longitudinal axis of the mouth-end section 502, and is thereby operable between first and second positions as described above with respect to the resilient member 450 described above with reference to FIG. 4.

However, the mouth-end section 502 illustrated in FIGS. 5a to 5d comprises a second resilient member 551. The second resilient member 551 is essentially the same as the first resilient member 550 described above, and so will not be described in detail. Similarly to the first resilient member 550, the second resilient member 551 is operable by a user to bend between a first position (as in FIG. 5b) in which the resilient member 551 does not extend into the channel 532, and a second position (as in FIG. 5c) in which it does.

The second resilient member 551 is located on an opposite side of the channel 532 to the first resilient member 550. The second resilient member 551 is located at the same position along the longitudinal axis P-P of the mouth-end section 502 to the first resilient member 550. The first resilient member 550 and the second resilient member 551 are thereby operable by a user to bend towards each other. A breakable flavor element 524 received in the channel 532 of the mouth-end section 502 may therefore be broken (e.g. crushed) between the first resilient member 550 and the second resilient member 551. There being two operable resilient members 550, 551 reduces the force required per resilient member 550, 551 to break (e.g. crush) the breakable flavor element 524 in the channel 532 there between. The two breaking elements 550, 551 being opposing allows for convenient manual operation of the resilient member 550, 551, for example using a thumb and an index finger of a user's hand, respectively.

The mouth-end section 502 comprises a resilient outer portion 553. The resilient outer portion 553 is generally annular in shape and surrounds the side wall 530, and the resilient members 550, 551 of the mouth-end section 502. The resilient outer portion 553, similarly to the resilient members 550, 551 is resilient in a direction substantially perpendicular to the longitudinal axis P-P of the mouth-end section 502. The resilient outer portion 553 comprises ribbing on its outer surface to facilitate a user's grip when squeezing laterally on the mouth-end section 502 to bend the resilient members 550, 551 when breaking (activating) the breakable flavor element 524 received in the channel 532. The resilient outer portion 553 is connected (e.g. fixedly connected) to the resilient members 550, 551 to bias the resilient members 550, 551 to the first position. It will be appreciated that the resilient outer portion 553 may have similar functionality as the reshaping elements 370, 371 described above with respect to FIG. 3, and this functionality will not be described again in detail. Suffice to say that the resilient outer portion 553 may help reshape the breakable flavor element after breaking by exerting a reshaping force along an axis perpendicular to the breaking axis.

Figure 5A:
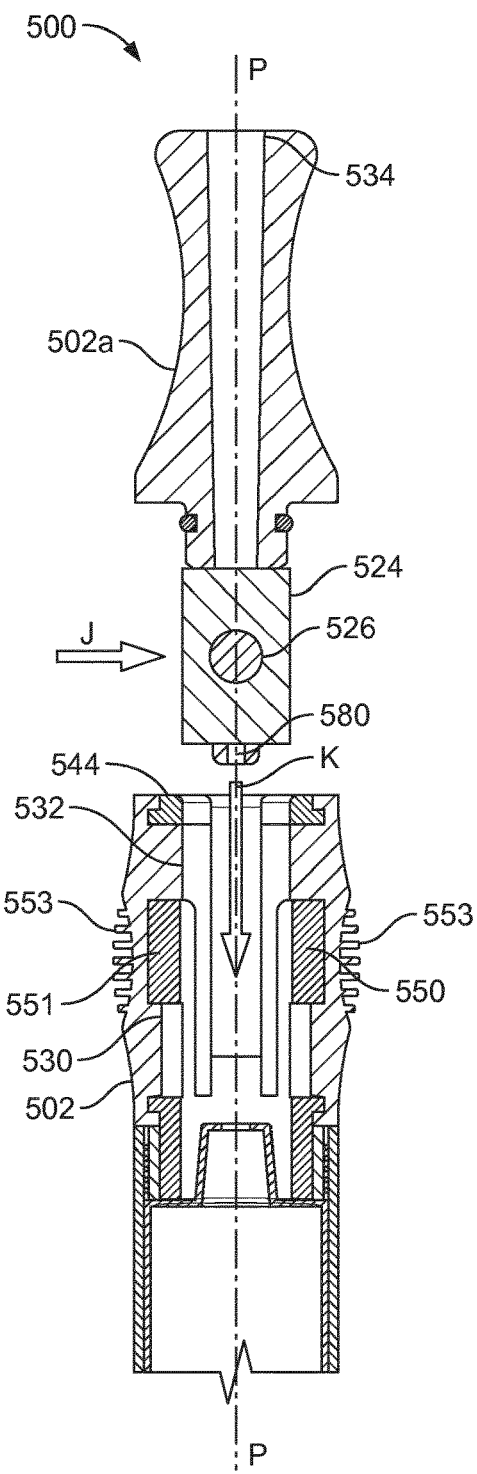
Figure 5B:
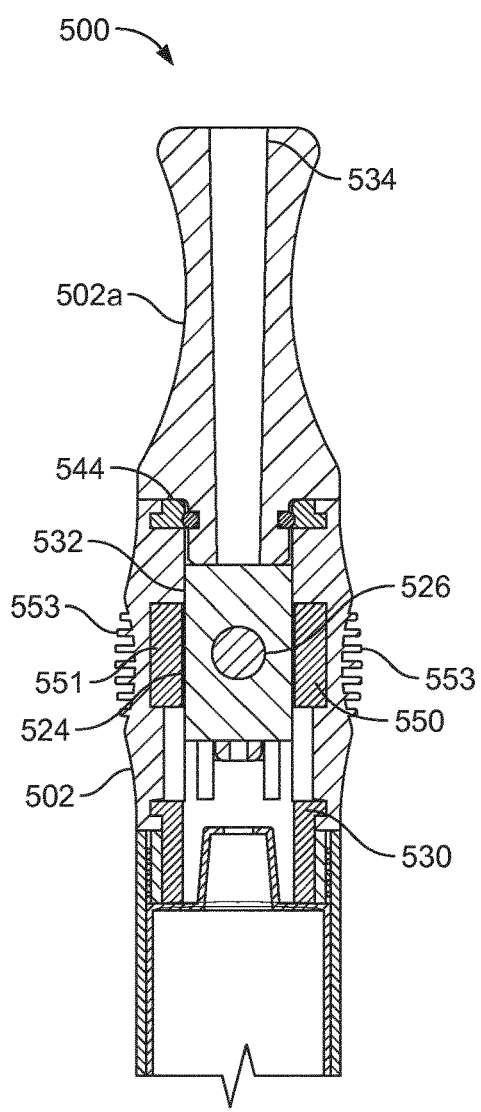
Figure 5C:
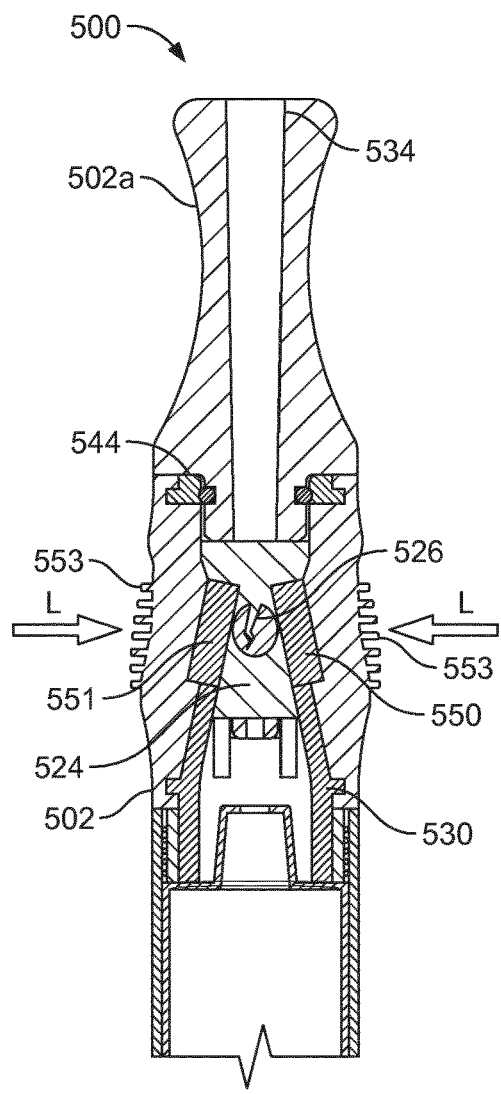
Figure 5D:
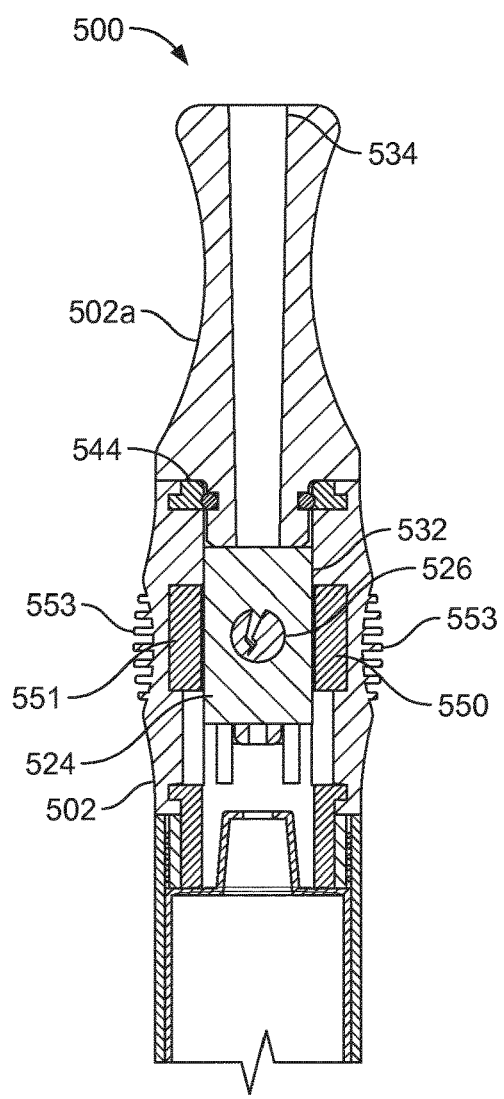

Referring to the sequence illustrated in FIGS. 5a to 5d, in FIG. 5a, the mouth portion 502a is removed from the mouth-end section 502, thereby to allow an insertion (arrow J) of the breakable flavor element 524 into a receiving portion 580 of the mouth portion 502a. A user may push (arrow K) the mouth portion 502a into the channel 532 of the mouth-end section 502, thereby installing the breakable flavor element 524 into the channel 532. In FIG. 5b, the breakable flavor element 524 is received in the channel 532, and the resilient members 551, 553 are in the first portion, i.e. parallel (unbent) with respect to the longitudinal axis P-P of the mouth-end section 502. At some later stage, a user may wish to break (activate) the breakable flavor element 524 so that aerosol inhaled from the device 500 is flavored there by. A user may therefore push (arrows L) laterally (i.e. in a direction substantially perpendicular to the longitudinal axis P-P of the mouth-end section 502) against the resilient members 550, 551, via the resilient outer portion 553. This causes the resilient members 550, 551 to bend inwards towards each other so as to protrude into the channel 532 and break the breakable flavor element 524, thereby releasing flavor from the breakable flavor capsule 526. The resilient member 550 is now in the second position (see FIG. 5c). When a user ceases to push on the resilient members 550, 551, due to the resilience (natural springiness) of the resilient members 550, 551, (or alternatively or additionally due to the resilience of the resilient outer portion 553 to which the resilient members 550, 551 are connected), the resilient members 550, 551 return to their respective first positions, i.e. return so as to be parallel (unbent) with respect to the longitudinal axis P-P of the mouth-end section 502 (FIG. 5d).

Figure 6A:
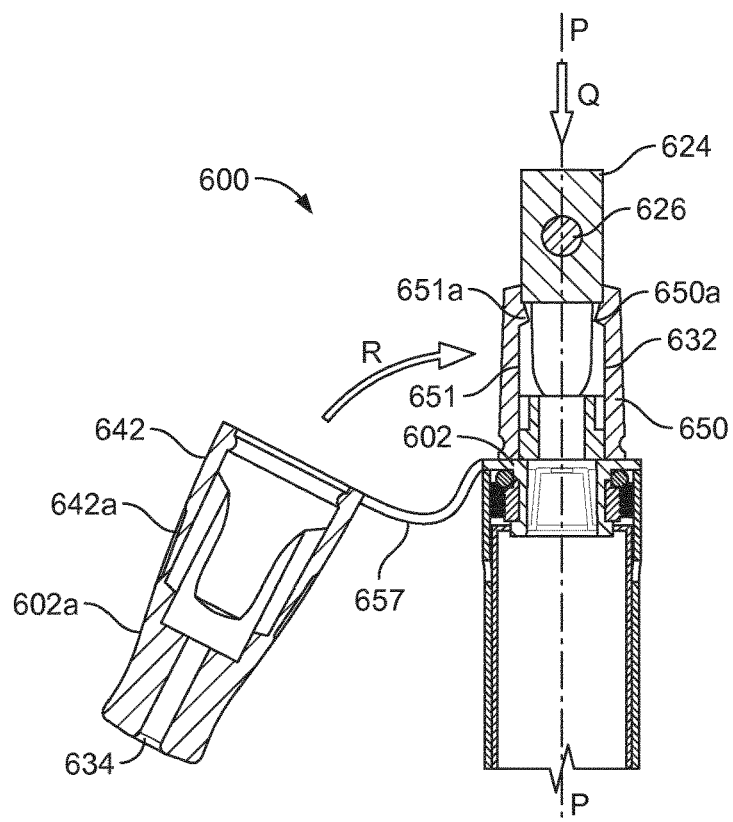
Figure 6B:
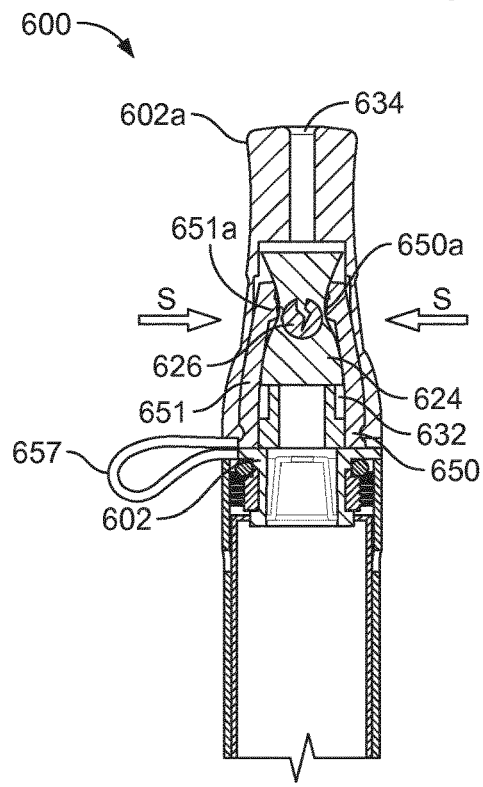
Figure 6C:
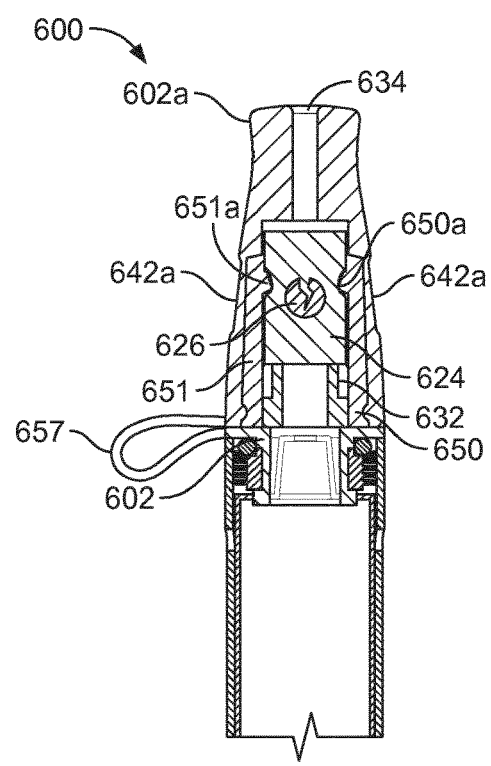

Referring now to FIGS. 6a to 6c, there is illustrated schematically cross sections of a part of an aerosol provision article 600 with another example receptacle section 602 in different configurations. In this example, the receptacle section is again a mouth-end section 602. For brevity, features in FIG. 6 and the functioning thereof that are the same or similar to those features already described with reference to FIGS. 5a to 5d are given similar reference numerals to as in FIG. 5 but increased by 100, and will not be described in detail again.

The mouth-end section 602 of FIGS. 6a to 6d is similar to the mouth-end section 502 illustrated in FIGS. 5a to 5d. The mouth-end section 602 comprises resilient members 650, 651 on opposite sides of a channel 632 that has a breakable flavor element 624 comprising a breakable flavor capsule 626, received therein. The resilient members 650, 651 are operably bendable into the channel 632, from the first position to the second position as described above with respect to FIGS. 5a to 5d, thereby to break the breakable flavor element 624.

However, in this example, the resilient members 650, 651 each comprise a respective inwardly protruding portion 650a, 651a that protrudes radially inwardly toward the channel 632, for breaking a breakable flavor element 624 received therein.

In this example, the resilient members 650, 651 are received in a mouth portion 602a for receipt into a user's mouth. The mouth portion 602a defines an opening 634 to allow a user to inhale aerosol from the device 600, via the channel 632. The mouth portion 602a is removable from the mouth-end section 602, thereby to expose the resilient members 650, 651, to allow a breakable flavor element 624 to be received there between. The mouth portion 602a is connected (tethered, leashed) to the mouth-end section 602 by a flexible leash 657. This leash 657 helps prevent the mouth portion 602a from being misplaced when removed from the mouth-end section 602.

A side wall 642 of the mouth portion 602a comprises a resilient portion 642a. The resilient portion 642a is generally annular in shape, and when the mouth portion 602a is connected to the mouth-end section 602 such that the resilient members 650, 651 are received in the mouth portion 602a, the resilient portion surrounds the resilient members 650, 651. Similarly to the resilient members 650, 651, the resilient portion 642a is resilient in a direction substantially perpendicular to the longitudinal axis P-P of the mouth-end section 602.

Referring to the sequence illustrated in FIGS. 5a to 5c, in FIG. 6a, the mouth portion 602a is removed from the mouth-end section 602, thereby to allow an insertion (arrow Q) of the breakable flavor element 624 into the channel 632, between the resilient members 650, 651. A user may manipulate (arrow R) the mouth portion 602a over the resilient members 650, 651 so as to connect the mouth portion 602a to the mouth-end section 602, thereby installing the breakable flavor element 624 into the mouth end section 602 (see FIG. 6a). At some later stage, a user may wish to break (activate) the breakable flavor element 624 so that aerosol inhaled from the device 600 is flavored there by. A user may therefore push (squeeze) (arrows S) laterally (i.e. in a direction substantially perpendicular to the longitudinal axis P-P of the mouth-end section 602) against the resilient members 650, 651, via the resilient portion 642a of the mouth portion 602a. This causes the resilient members 650, 651 to bend inwards towards each other so as to protrude into the channel 632 and break, via the respective inward protruding portions 650a, 651a, the breakable flavor element 624, thereby releasing flavor from the breakable flavor capsule 626. The resilient members 650, 651 are now in the second position (see FIG. 6b). When a user ceases to push on the resilient members 650, 651, due to the resilience (natural springiness) of the resilient members 650, 651, the resilient members 650, 651 return to their respective first positions, i.e. return so as to be parallel (unbent) with respect to the longitudinal axis P-P of the mouth-end section 502 (FIG. 6c).

Referring now to FIGS. 7a to 7d, there is illustrated schematically cross sections of a part of an aerosol provision article 700 with another example receptacle section 702 in different configurations. In this example, the receptacle section is again a mouth-end section 702. For brevity, features in FIG. 7 and the functioning thereof that are the same or similar to those features already described with reference to FIGS. 6a to 6c are given similar reference numerals to as in FIG. 6 but increased by 100, and will not be described in detail again.

The mouth-end section 702 of FIGS. 7a to 7d is similar to the mouth-end section 502 illustrated in FIGS. 6a to 6c. The mouth-end section 702 comprises resilient members 750, 751 on opposite sides of a channel 732 that has a breakable flavor element 724 comprising a breakable flavor capsule 726, received therein. The resilient members 750, 751 are operably bendable into the channel 732, from the first position to the second position as described above with respect to FIGS. 6a to 6c, thereby to break the breakable flavor element 724.

However, unlike the resilient members 650, 651 described with reference to FIGS. 6a to 6c, the resilient members 750, 751 are not bent together laterally by a user applying a lateral squeezing force to the resilient members 750, 751, but are bent together by the sliding of an operation element 759 substantially parallel to the longitudinal axis P-P of the mouth-end section 702.

Specifically, the mouth portion 702a of the mouth-end section 702, when installed in the mouth-end section 702, is a housing 702a in which the resilient members 750, 751 and the breakable flavor element 724 is housed. The operation element 759 is slidably mounted to the mouth portion 702a thereby allowing sliding movement of the operation element 759 relative to the mouth portion 702a substantially parallel to the longitudinal axis P-P of the mouth-end section 702. In this example, the operation element 759 is generally annular in shape and is arranged around a circumference of the mouth portion as a collar 759.

The resilient members 750, 751 each comprise an outward protruding portion 750b, 751b. The outward protruding portion 750b, 751b protrude out from the respective resilient member 750, 751 away from the channel 732, and are for contacting the operation element 759 of the mouth-end section 702.

Figure 7C:
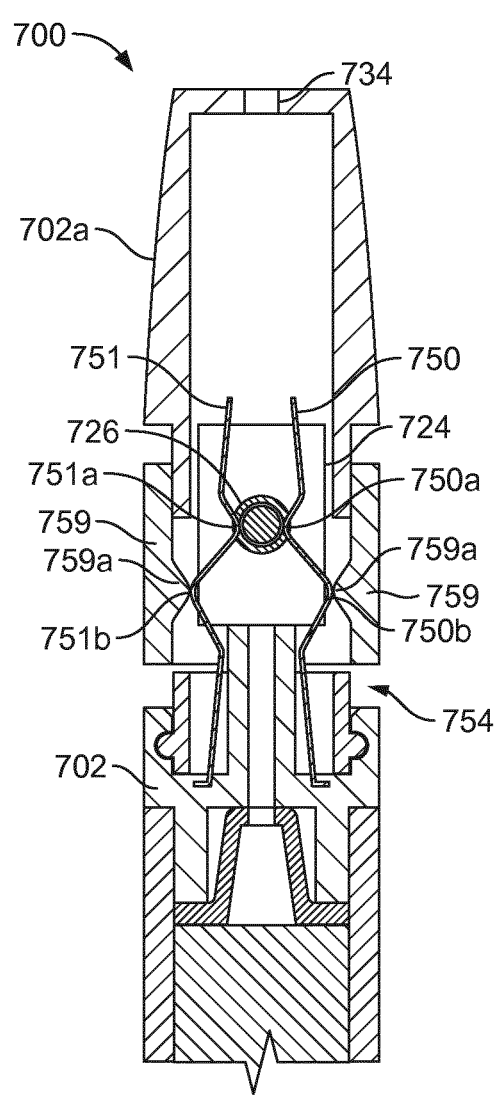

The operation element 759 is operable by a user to slide between a first operation element position (see FIG. 7b) and a second operation element position (see FIG. 7c). In the first operation element position (FIG. 7b) the operation element 759 is positioned relatively away from (i.e. axially distant from) the outward protruding portion 750b, 751b of the resilient member 750, 751. In this position, the operation element 759 does not exert any radially inward force on the resilient member 750, 751, and the resilient member 750, 751 remains in the first position. In the second operation element position (FIG. 7c) the operation element 759 is positioned relatively towards (i.e. axially proximal to) the outward protruding portion 750b, 751b of the resilient member 750, 751. In this position, the operation element 759 displaces the outward protruding portion 750b, 751b and hence the resilient member 750, 751 radially inwardly towards the channel 732, i.e. to the second position. Sliding of the operation element 759 relative to the mouth portion 702a substantially parallel to the longitudinal axis P-P of the mouth-end section 702, from the first operation element position (FIG. 7b) to the second operation element position (FIG. 7c), thereby causes bending of the resilient member 750 from the first position to the second position, thereby breaking said breakable flavor element 724 received in the channel 732.

The operation element 759 comprises an inward protruding portion 759a protruding out of the operation element 759 towards the resilient member 750, 751. When the operation element 759 is in the second operation element position (FIG. 7b), the inward protruding portion 759a of the operation element 759 is longitudinally (axially) aligned with the outward protruding portion 750b, 751b of the resilient member 750, 751. The inward protruding portion 759a of the operation element 759 thereby increases the displacement (bending) of the resilient members 750, 751 into the channel 732, and thereby provides efficient breaking of the breakable flavor element 724 received in the channel 732.

Figure 7D:
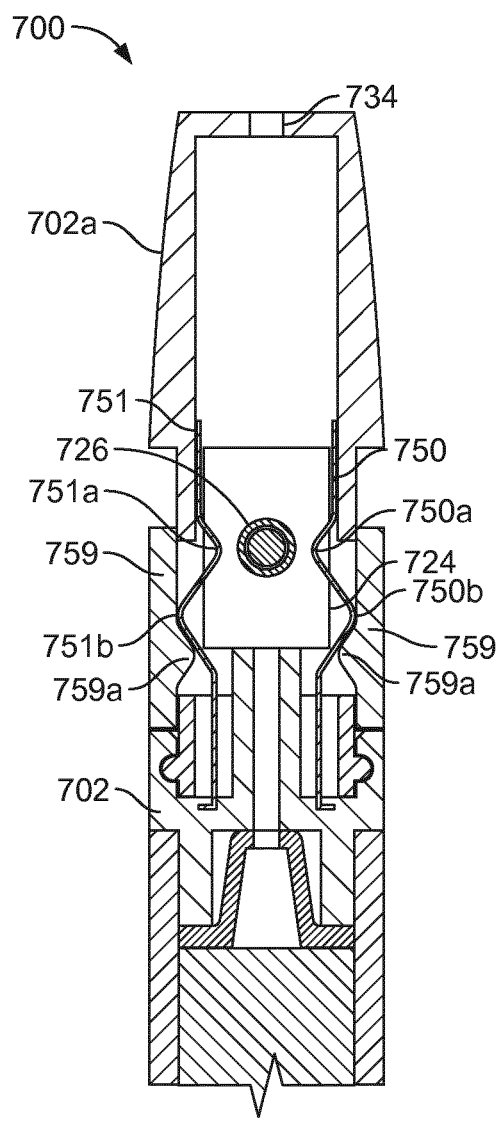

The operation element 759 is slidable beyond the second operation element position to a third operation element position (see FIG. 7d). In the third operation element position, the inward protruding portion 759a of the operation element 759 is slid beyond, and hence longitudinally (axially) misaligned with the outward protruding portion 750b, 751b of the resilient member 750, 751. In this position, as with the first operation element position, the operation element 759 does not exert any radially inward force on the resilient member 750, 751, and the resilient member 750, 751 returns again by virtue of its resilience (natural springiness) to the first position. In this example, the operation element 759 in the third operation element position closes off a gap 754 in the mouth portion 702a, thereby to seal the flow path through the mouth-end section 702 from the body 706 of the overall device 700 to the outlet 734 of the mouth portion 734.

Referring to the sequence illustrated in FIGS. 7a to 7d, in FIG. 7a, the mouth portion 702a is removed from the mouth-end section 702, thereby to allow an insertion of the breakable flavor element 724 between the resilient members 750, 751. A user may attach the mouth portion 702a to the mouth-end section 702, thereby housing the resilient members 750, 751 and the breakable flavor element 724 in the mouth portion 702a (see FIG. 7b). In FIG. 7b, the operation element 759 is in the first operation element position, and hence the resilient members 751, 750 are in the first position, i.e. parallel (unbent) with respect to the longitudinal axis P-P of the mouth-end section 702. At some later stage, a user may wish to break (activate) the breakable flavor element 724 so that aerosol inhaled from the device 700 is flavored thereby. A user may therefore push, pull, or otherwise manipulate the operation element 759 relative to the mouth-end section 702 towards the body 706 of the device 700 in a direction substantially parallel to the longitudinal axis P-P of the mouth-end section 702. This causes the inward protruding portions 759a of the operation element 759 to push against the outward protruding portion 750b, 751b of the resilient members. This pushing results in a radially inward force that causes the resilient members 750, 751 to bend inwards towards each other so as to protrude into the channel 732 and break the breakable flavor element 724, thereby releasing flavor from the breakable flavor capsule 726 (see FIG. 7c). The operation element 759 is now in the second operation element position, and the resilient members 750, 751 are now in the second position (see FIG. 7c). A user may continue to push, pull, or otherwise manipulate the operation element 759 relative to the mouth-end section 702 further towards the body 706 of the device 700 in a direction substantially parallel to the longitudinal axis P-P of the mouth-end section 702, until the operation element 759 is in the third operation element position (FIG. 7d). The resilient members 750, 751 are therefore no longer displaced by the operation element 759. Due to the resilience (natural springiness) of the resilient members 750, 751, the resilient members 750, 751 return to their respective first positions, i.e. return so as to be substantially parallel (unbent) with respect to the longitudinal axis P-P of the mouth-end section 702 (FIG. 7d).

Figure 8A:
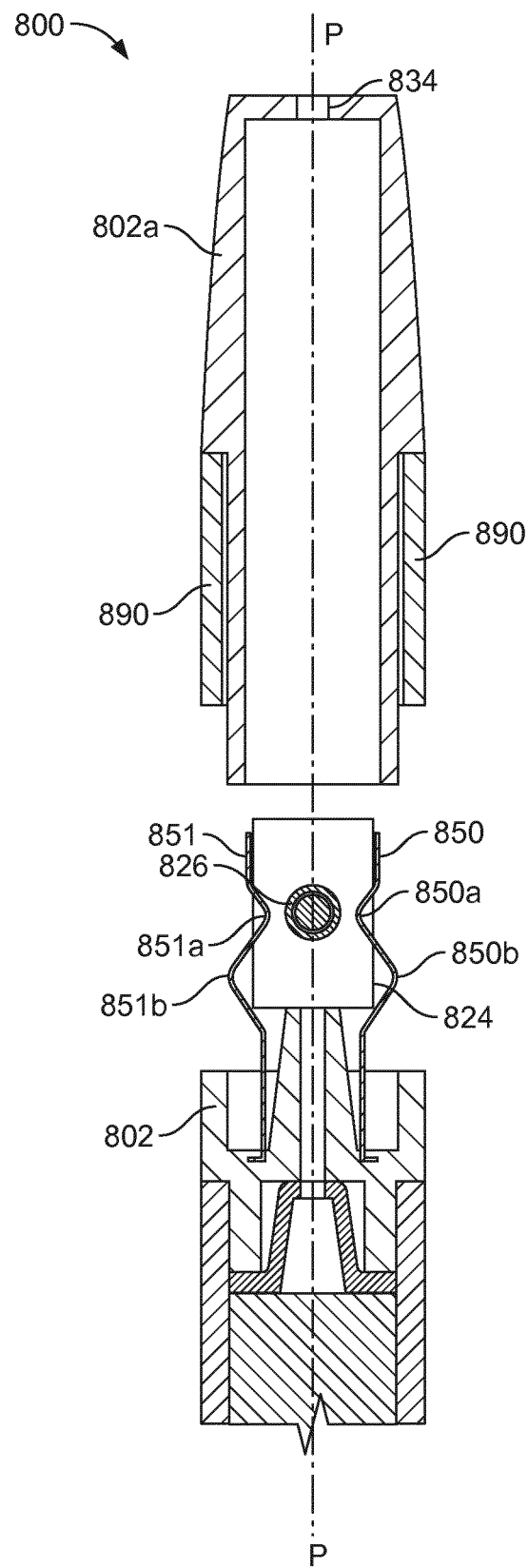
Figure 8B:
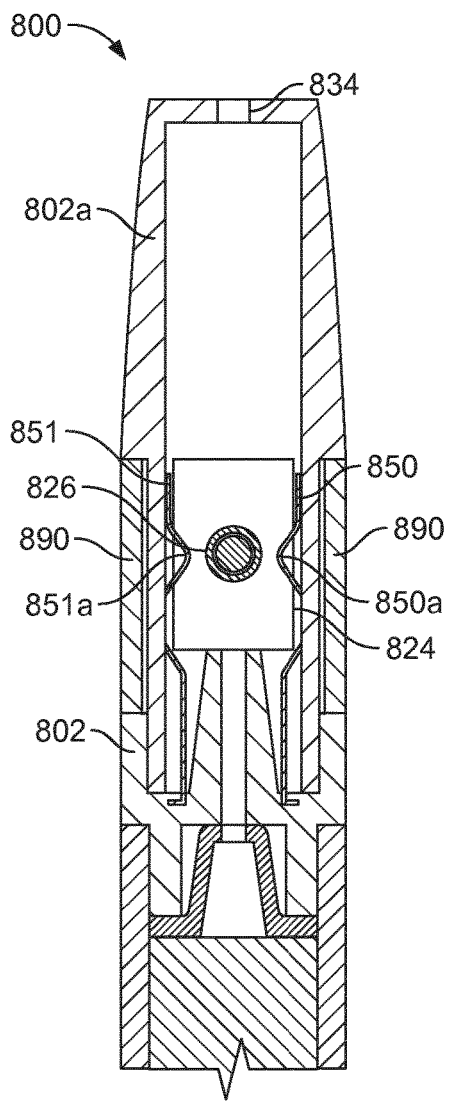
Figure 8C:
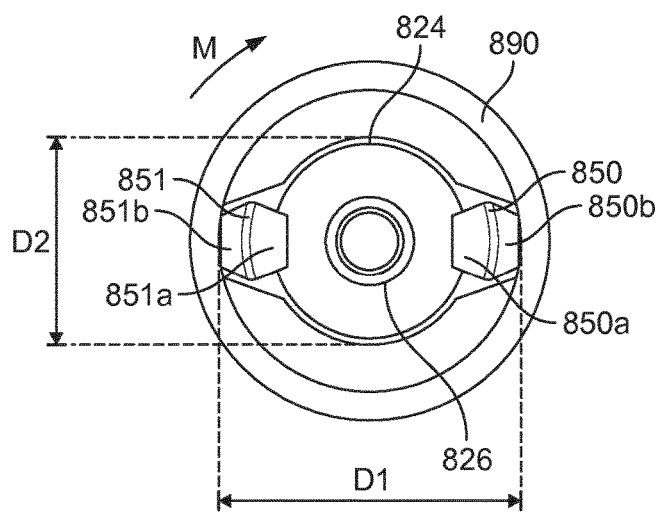
Figure 8D:
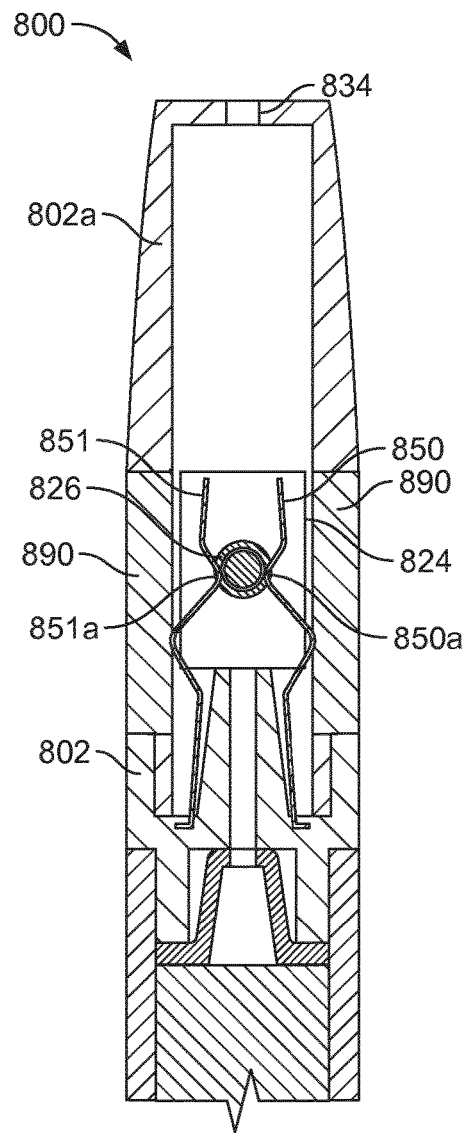

Referring now to FIGS. 8a to 8e, there is illustrated schematically cross sections of a part of an aerosol provision article 800 with another example receptacle section 802 in different configurations. The cross sections of FIGS. 8c and 8e correspond to the cross sections of FIGS. 8b and 8c respectively, but the cross sections 8c and 8e are taken in a plane perpendicular to the plane in which FIGS. 8b and 8c are presented, respectively. In this example, the receptacle section 802 is again a mouth-end section 802. For brevity, features in FIG. 8 and the functioning thereof that are the same or similar to those features already described with reference to FIGS. 7a to 7d are given similar reference numerals to as in FIGS. 7a to 7d but increased by 100, and will not be described in detail again.

The mouth-end section 802 of FIGS. 8a to 8e is similar to the mouth-end section 702 illustrated in FIGS. 7a to 7d. The mouth-end section 702 comprises resilient members 850, 851 on opposite sides of a channel 832 that has a breakable flavor element 824 comprising a breakable flavor capsule 826, received therein. The resilient members 850, 851 are operably bendable by an operation element 890 into the channel 832, from the first position to the second position as described above with respect to FIGS. 8a to 8d, thereby to break the breakable flavor element 824. The resilient members 850, 851 each comprise an outward protruding portion 850b, 851b protruding out from the respective resilient member 850, 851 away from the channel 832 for contacting the operation element 890.

However, unlike the resilient members 750, 751 described with reference to FIGS. 7a to 7d, the resilient members 850, 851 are not bent together laterally by the sliding of an operation element 759 substantially parallel to the longitudinal axis P-P of the mouth-end section 702, but are bent together laterally by the rotation of an operation element 890 about the longitudinal axis P-P of the mouth-end section 802.

Specifically, the mouth portion 802a of the mouth-end section 802, when installed in the mouth-end section 802, is a housing 802a in which the resilient members 850, 851 and the breakable flavor element 824 is housed. The operation element 890 is rotatably mounted to the mouth portion 802a thereby allowing rotation of the operation element 890 relative to the mouth portion 802a about the longitudinal axis P-P of the mouth-end section. In this example, the operation element 890 is generally annular in shape and is arranged around a circumference of the mouth portion as a collar 890.

Figure 8E:
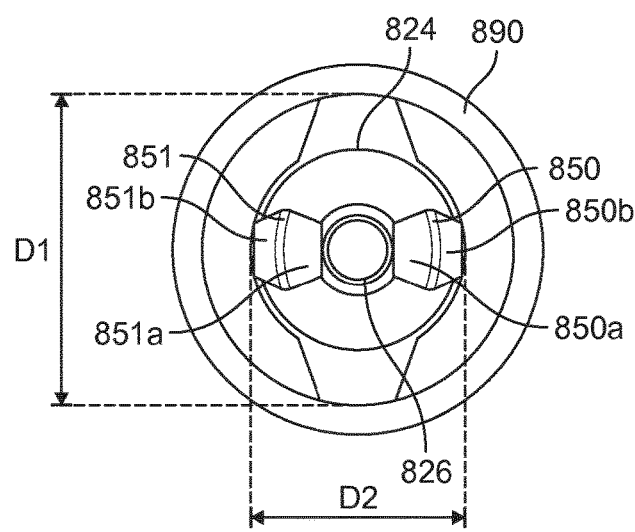

The operation element 890 defines a first inner radial dimension D1 and a second, smaller inner radial dimension D2 (best seen in FIGS. 8c and 8e). The operation element 890 is operable by a user to rotate relative to the moth portion 802a about the longitudinal axis P-P of the mouth-end section 802 between a first operation element orientation (see FIGS. 8b and 8c)) and a second operation element orientation (see FIGS. 8d and 8e). In the first operation element orientation (FIGS. 8b and 8c) the first inner radial dimension D1 is rotationally aligned with the resilient member 850, 851. In this orientation, the resilient members 850, 851 experience the larger inner radial dimension D1 of the operation element. The inner radial dimension is larger than the distance between the outward protruding portions 850b, 851b of the respective resilient members 850, 851 when substantially parallel to the longitudinal axis P-P of the mouth-end section 802, and so the operation element 890 does not displace the resilient members 850, 851. The resilient members 850, 851 therefore remain in the first position. In the second operation element orientation (FIGS. 8d and 8e) the second inner radial dimension D2 is rotationally aligned with the resilient member 850, 851. In this orientation, the resilient members 850, 851 experience the smaller inner radial dimension D2 of the operation element 890. The second inner radial dimension D2 is smaller than the distance between the outward protruding portions 850b, 851b of the resilient members 850, 851 when substantially parallel to the longitudinal axis P-P of the mouth-end section 802, and so the operation element 890 displaces the resilient members 850, 851 inwardly towards the breakable flavor element 824. The resilient members 850, 851 are therefore forced to the second position, and inwardly protruding portions 850a, 851a of resilient members 850, 851 contact and break the breakable flavor element 824 received there between. Rotation of the operation element 890 relative to the mouth portion 802a about the longitudinal axis P-P of the mouth-end section 802, from the first operation element orientation (FIGS. 8b and 8c) to the second operation element orientation (FIGS. 8d and 8e), thereby causes bending of the resilient members 850, 851 from the first position to the second position, thereby breaking said breakable flavor element 824 received in the channel 832.

The first radial dimension D1 is oriented at right angles about the longitudinal axis P-P of the mouth-end section 802 with respect to the second radial dimension D2. In this case, in order to change from the first operation element orientation to the second operation element orientation, a user rotates the operation element 890 a quarter turn (i.e. by 90°) about the longitudinal axis P-P of the mouth-end section 802.

As best seen in FIGS. 8c and 8e, the inner radial dimension of the operation element 890 varies gradually from the first inner radial dimension D1 to the second inner radial dimension D2. That is, there is not a step change in the inner radial dimension of the operation element 890, but rather a gradual increase from small to large at successive points around the circumference of the operation element 890. This gradual increase (or 'gearing') provides a reduction in the degree to which the resilient members 850, 851 are bent for a given degree of rotation of the operation element 890 about the longitudinal axis. This 'gearing' can reduce the torque required to be exerted on the operation element 890 to break the breakable flavor element 824, and hence provides for easy and convenient breaking of a breakable flavor element 824 installed into an overall device 800.

Referring to the sequence illustrated in FIGS. 8a to 8e, in FIG. 8a, the mouth portion 802a is removed from the mouth-end section 802, thereby to allow an insertion of the breakable flavor element 824 between the resilient members 850, 851. A user may attach the mouth portion 802a to the mouth-end section 802, thereby housing the resilient members 850, 851 and the breakable flavor element 824 in the mouth portion 802a (see FIG. 8b). In FIGS. 8b and 8c, the operation element 890 is in the first operation element orientation, and hence the resilient members 851, 850 are in the first position, i.e. parallel (unbent) with respect to the longitudinal axis P-P of the mouth-end section 802. At some later stage, a user may wish to break (activate) the breakable flavor element 824 so that aerosol inhaled from the device 800 is flavored there by. A user may therefore rotate (arrow M) the operation element 890 relative to the mouth-end section 802 about the longitudinal axis P-P of the mouth-end section 802 by 90°. This causes the inner surface of the operation element 890 at the second radial dimension D2 to push against the outward protruding portion 850b, 851b of the resilient members. This pushing results in a radially inward force that causes the resilient members 850, 851 to bend inwards towards each other so as to protrude into the channel 832 and break the breakable flavor element 824, thereby releasing flavor from the breakable flavor capsule 826 (see FIGS. 8d and 8e). The operation element 890 is now in the second operation element orientation, and the resilient members 850, 851 are now in the second position (see FIGS. 8d and 8e). A user may continue to rotate the operation element 890 (or alternatively rotate the operation element back) until the operation element 890 is back in the first operation element orientation (as in FIGS. 8b and 8c). The resilient members 850, 851 are therefore no longer displaced by the second inner radial dimension D2 of the operation element 890. Due to the resilience (natural springiness) of the resilient members 850, 851, the resilient members 850, 851 return to their respective first positions, i.e. return so as to be parallel (unbent) with respect to the longitudinal axis P-P of the mouth-end section 802 (as in FIGS. 8b and 8c).

Although in the examples described above the various receptacle sections 102, 202, 302, are generally described as being arranged to break a breakable flavor element 124, 224, 324, etc., by crushing a flavor capsule 126, 226, 326, etc., it will be appreciated that there are other ways in which a flavor element 124, 224, 324, etc., may be broken. For example, alternatively or in addition, the receptacle sections 102, 202, 302 may break a flavor element 124, 224, 324, etc., by piercing, puncturing, cutting, or slicing a flavor capsule 126, 226, 326. of a flavor element 124, 224, 324, etc. For example, breaking elements (such as for example resilient members 250, 251, 350, 351, etc. or inwardly protruding portions 560, 660, etc.) may comprise a spike or other sharp protrusion for piercing or puncturing a flavor capsule 126, 226, 326, or an edge for cutting or slicing a flavor capsule 126, 226, 326, etc., of a flavor element 124, 224, 324 etc. for example.

Although in the examples described above the various receptacle sections 102, 202, 302, were described as being arranged to break a breakable flavor element 124, 224, 324, etc., after an installation of the breakable flavor element 124, 224, 324, etc., into the receptacle section, this is not essential, and the various receptacle sections 102, 202, 302 may be arranged to activate any suitable activatable element 124, 224, 324, etc., by applying a force to activate the activatable element 124, 224, 324, etc., after an installation of the activatable element 124, 224, 324, etc., into the receptacle section 102, 202, 302, etc. In other words, rather than at least one breaking element operable to break a breakable flavor element, the receptacle section may comprise at least one activating element operable to apply, after an installation of said activatable element in the receptacle section by a user, a force to the activatable element to activate the activatable element.

In some examples, the activatable element may comprise a reservoir of flavorant (for example in the form of a liquid and/or gel). The reservoir may be wrapped or embedded in a suitable carrier material, such as cellulose acetate. The reservoir may have resilient or deformable walls. The reservoir may have an aperture allowing flavorant to be released from the reservoir to the carrier material. When a force is applied to the activatable element by an activating element of a receptacle section as described in detail in any one of the various above examples (for example via breaking elements such as resilient members 250, 350, 351, 450, etc.), the reservoir is squeezed (deformed) and the flavorant is thereby forced from the reservoir through the aperture into the carrier material. The receptacle section thereby activates an activatable flavor element by applying a force, after an installation of the activatable flavor element into the receptacle section, to the activatable element.

In some examples, the activatable element may comprise flavor material, for example solid material, which when ground, exposed, or otherwise suitably physically activated, releases a flavorant. The flavor material may be, for example, ground tobacco. The flavor material may be for example wrapped partially or wholly in a wrapper, and/or the flavor material may be supported in a resilient housing, for example a plastic housing, or may be held or embedded in a suitable carrier material such as cellulose acetate. When a force is applied to the activatable element by a receptacle section as described in detail in any one of the various above examples above (for example via resilient members 250, 350, 351, 450, etc.), the solid material is exposed or otherwise suitably physically activated, and a flavorant (or an increase and/or change in flavorant) is released thereby to impart a flavor (or increased and/or different flavor) to the aerosol flow. The receptacle section thereby activates an activatable flavor element by applying, after an installation of the activatable flavor element into the receptacle section, a force to activate the activatable element.

Although in the examples described above, the activatable element 124, 224, 324, etc., received in the various receptacle sections 202, 302, 402, etc., is a flavor element 124, 224, 324 etc. and is for releasing a flavorant to impart a flavor to the aerosol when the aerosol flows through the flavor element 124, 224, 324, etc., this is not essential and instead (or in addition) the activatable element 124, 224, 324, etc., may be for modifying a property of the aerosol other than (or in addition) to flavor, for example comprise a substance for modifying a property of the aerosol other than (or in addition) to flavor.

In some examples, the element 124, 224, 324 etc. may comprise a substance that modifies one or more other organoleptic properties of the aerosol (e.g. modifying the feel or smell or look of the aerosol to the user).

In some examples, the element 124, 224, 324, etc., may comprise a substance that modifies the PH of the aerosol by either lowering or raising the PH (e.g. modifying the acidity or the basicity of the aerosol).

In some examples, the element 124, 224, 324, etc., may comprise a substance that modifies (e.g. reduce) the amount of aldehydes in the aerosol.

In some examples, the element 124, 324, 324 etc. may comprise a substance that modifies different combinations of two or more of these or indeed other properties of the aerosol.

Although in the above described examples, the device 100, 200, 300, etc., generates the aerosol by heating a liquid (the device is of type commonly referred to as an e-cig), this is not essential and in other examples, the device may generate the aerosol by heating, but not burning (combusting), a material, for example comprising a solid material, that may contain for example tobacco (e.g. a device sometimes referred to as a Tobacco Heating Product (THP) device).

In the above examples, the liquid container 122 was cylindrical in shape and defined a cylindrical channel 104 running through the length of the liquid container 122. However, in other examples, the liquid container may not be annular in shape, and/or the liquid container may comprise an outer shell that defines an annular channel between the liquid container and the outer shell through which vapor or aerosol may also, or instead, pass.

Indeed, it will be readily appreciated that there are many configurations of aerosol provision articles such as so called e-cigarette devices (some of which not having refillable liquid containers integral to the device as such, but rather, for example, replaceable cartridges, for example comprising integral atomizers, i.e. so called "cartomizers") and that the above examples may also be applied to these or other configurations or to other aerosol provision articles.

In use, the material of the flavor element may be heated by vapor or aerosol with a temperature higher than the temperature of the material. It will be appreciated that any temperature above ambient temperature of the material and/or above the ambient temperature of the device as a whole will improve release of constituents from the solid material.

As used herein, the terms "flavor" and "flavorant" may refer to materials which, where local regulations permit, may be used to create a desired taste or aroma in a product for adult consumers. They may include extracts (e.g., licorice, hydrangea, Japanese white bark magnolia leaf, chamomile, fenugreek, clove, menthol, Japanese mint, aniseed, cinnamon, herb, wintergreen, cherry, berry, peach, apple, Drambuie, bourbon, scotch, whiskey, spearmint, peppermint, lavender, cardamom, celery, cascarilla, nutmeg, sandalwood, bergamot, geranium, honey essence, rose oil, vanilla, lemon oil, orange oil, cassia, caraway, cognac, jasmine, ylang-ylang, sage, fennel, piment, ginger, anise, coriander, coffee, or a mint oil from any species of the genus Mentha), flavor enhancers, bitterness receptor site blockers, sensorial receptor site activators or stimulators, sugars and/or sugar substitutes (e.g., sucralose, acesulfame potassium, aspartame, saccharine, cyclamates, lactose, sucrose, glucose, fructose, sorbitol, or mannitol), and other additives such as charcoal, chlorophyll, minerals, botanicals, or breath freshening agents. They may be imitation, synthetic or natural ingredients or blends thereof. They may be in any suitable form, for example, oil, liquid, solid, or powder. For example, a liquid, oil, or other such fluid flavorant may be impregnated in a porous solid material so as to impart flavor and/or other properties to that porous solid material. As such, the liquid or oil is a constituent of the material in which it is impregnated.

The above embodiments are to be understood as illustrative examples of the invention. It is to be understood that any feature described in relation to any one embodiment may be used alone, or in combination with other features described, and may also be used in combination with one or more features of any other of the embodiments, or any combination of any other of the embodiments. Furthermore, equivalents and modifications not described above may also be employed without departing from the scope of the invention, which is defined in the accompanying claims.

The invention claimed is:

1. An aerosol provision article for generating a flow of aerosol in use, the aerosol provision article comprising a receptacle section arranged for receiving therein an activatable element for modifying, once activated, a property of the flow of aerosol, the receptacle section comprising:
   a channel for having the activatable element removably installed therein, and
   at least one activating element operable to apply, after installing the activatable element in the channel of the receptacle section by a user, a force to the activatable element to activate, the activatable element installed in the receptacle section in use,
   wherein the at least one activating element is moveable between a first position and a different, second position for activating the activatable element installed in the receptacle section in use,
   wherein the first position is for allowing removable installation of the activatable element in the channel of the receptacle section by a user, when the receptacle section is connected to the aerosol provision article, and
   wherein movement of the at least one activating element from the first position to the second position causes the force to be applied to activate the activatable element installed in the receptacle section in use, wherein the at least one activating element is slidably mounted through a side wall of the receptacle section and is operable by a user to slide between the first position and the second position, and wherein in the second position the at least one activating element extends into the channel thereby to apply the force to activate the activatable element received in the channel in use.

2. The aerosol provision article according to claim 1, wherein the movement comprises movement of the at least one activating element along an axis substantially perpendicular to a longitudinal axis of the receptacle section.

3. The aerosol provision article according to claim 2, wherein the at least one activating element comprises a resilient member extending along at least a portion of the channel, and wherein the resilient member is operable to bend between the first position and the second position, wherein in the second position at least a portion of the resilient member protrudes into the channel, thereby to apply the force to activate the activatable element received in the channel in use.

4. The aerosol provision article according to claim 3, wherein either:

an end of the at least one resilient member is free to move relative to the receptacle section; or the resilient member comprises an inwardly protruding portion protruding from the resilient member towards the channel, the inwardly protruding portion being for contacting the activatable element received in the channel in use, thereby to apply the force to activate the activatable element received in the channel in use.

5. The aerosol provision article according to claim 3, wherein the resilient member comprises an outwardly protruding portion, the outwardly protruding portion protruding out from the resilient member away from the channel, and being for contacting an operation element of the receptacle section.

6. The aerosol provision article according to claim 5, wherein the receptacle section comprises a housing in which the at least one resilient member and the activatable element are housed, wherein the operation element is slidably mounted to the housing thereby allowing sliding movement of the operation element relative to the housing substantially parallel to a longitudinal axis of the receptacle section, the operation element being operable by a user to slide between a first operation element position in which the operation element is positioned relatively away from the outwardly protruding portion of the resilient member, and a second operation element position in which the operation element is positioned relatively towards the outwardly protruding portion of the resilient member, wherein sliding of the operation element from the first operation element position to the second operation element position causes bending of the resilient member from the first position to the second position, thereby applying the force to activate the activatable element received in the channel in use.

7. The aerosol provision article according to claim 6, wherein the operation element comprises an inwardly protruding portion protruding out of the operation element towards the resilient member, wherein when the operation element is in the second operation element position, the inwardly protruding portion of the operation element is longitudinally aligned with the outwardly protruding portion of the resilient member.

8. The aerosol provision article according to claim 3, wherein the receptacle section comprises a housing in which the resilient member is housed and the activatable element is housable, wherein the receptacle section comprises an operation element, the operation element being rotatably mounted to the housing thereby allowing rotation of the operation element relative to the housing about the longitudinal axis of the receptacle section, the operation element defining a first inner radial dimension and a second, smaller inner radial dimension, the operation element being operable by a user to rotate between a first operation element orientation in which the first inner radial dimension is rotationally aligned with the resilient member, and a second operation element orientation in which the second inner radial dimension is rotationally aligned with the resilient member, wherein rotation of the operation element from the first operation element orientation to the second operation element orientation causes said bending of the resilient member from the first position to the second position, thereby applying the force to activate the activatable element received in the channel in use.

9. The aerosol provision article according to claim 8, wherein the inner radial dimension of the operation element varies gradually from the first inner radial dimension to the second inner radial dimension.

10. The aerosol provision article according to claim 3, wherein either:
  the receptacle section comprises a resilient outer portion, wherein the resilient outer portion is connected to the resilient member to bias the resilient member to the first position; or
  the receptacle section comprises at least two resilient members, a first resilient member being located on an opposite side of the channel to a second resilient member.

11. The aerosol provision article according to claim 1, wherein the receptacle section comprises at least one reshaping element extending along at least a portion of the channel, wherein the reshaping element is moveable in a direction substantially perpendicular to the longitudinal axis of the receptacle section and biased towards the channel, thereby allowing reshaping of the activatable element received in the channel after a deformation due to the activation of the activatable element in use.

12. The aerosol provision article according to claim 11, wherein either:
  the at least one reshaping element is oriented at or near a right angle about the longitudinal axis of the receptacle section with respect to one of the at least one activating element; or
  the receptacle section comprises at least two activating elements, and at least two reshaping elements, wherein a first activating element is located on an opposite side of the channel to a second activating element, and wherein a first reshaping element is located on an opposite side of the channel to a second reshaping element.

13. The aerosol provision article according to claim 1, wherein the activatable element is installed in the receptacle section.

14. The aerosol provision article according to claim 13, wherein the activatable element comprises a substance for modifying the property of the aerosol, and the force causes the substance to be exposed, thereby to modify the property of the flow of aerosol.

15. The aerosol provision article according to claim 1, wherein the property is one or more of an organoleptic property of the aerosol, a flavor of the aerosol, or a pH of the aerosol.

16. The aerosol provision article according to claim 1, wherein the receptacle section comprises a connecting portion for releasably connecting the receptacle section to the aerosol provision article.

17. The aerosol provision article according to claim 1, further comprising a mouthpiece comprising the receptacle section.

18. The aerosol provision article according to claim 1, comprising:
  a container for holding a liquid or a material; and
  a heater for volatilizing liquid held in the container to generate the flow of aerosol in use or for heating but not combusting the material to generate the flow of aerosol in use.

* * * * *